(12) United States Patent
Vardi

(10) Patent No.: US 11,412,941 B2
(45) Date of Patent: Aug. 16, 2022

(54) SYSTEM AND METHOD FOR CALIBRATING A REMOTE BLOOD PRESSURE SYSTEM

(71) Applicant: ETROG SYSTEMS LTD., Kiryat Gat (IL)

(72) Inventor: Eyal Dov Vardi, Bet-Nir (IL)

(73) Assignee: ETROG SYSTEMS LTD., South District (IL)

(*) Notice: Subject to any disclaimer, the term of this patent is extended or adjusted under 35 U.S.C. 154(b) by 0 days.

(21) Appl. No.: 16/945,030

(22) Filed: Jul. 31, 2020

(65) Prior Publication Data

US 2020/0390349 A1 Dec. 17, 2020

Related U.S. Application Data

(63) Continuation-in-part of application No. 16/356,680, filed on Mar. 18, 2019, now Pat. No. 11,154,195.

(60) Provisional application No. 62/643,912, filed on Mar. 16, 2018.

(51) Int. Cl.
| | |
|---|---|
| *A61B 5/02* | (2006.01) |
| *A61B 5/021* | (2006.01) |
| *A61B 5/022* | (2006.01) |
| *A61B 5/024* | (2006.01) |
| *A61B 5/00* | (2006.01) |
| *G16H 10/60* | (2018.01) |
| *A61B 5/25* | (2021.01) |

(52) U.S. Cl.
CPC .......... *A61B 5/02125* (2013.01); *A61B 5/022* (2013.01); *A61B 5/02141* (2013.01); *A61B 5/02416* (2013.01); *A61B 5/25* (2021.01); *A61B 5/746* (2013.01); *G16H 10/60* (2018.01); *A61B 2560/0223* (2013.01)

(58) Field of Classification Search
CPC . A61B 5/02125; A61B 5/02141; A61B 5/022; A61B 5/02416; A61B 5/25; A61B 5/746; A61B 2560/0223; A61B 5/0022; G16H 10/60; G16H 40/67; G16H 40/40
USPC ....................................................... 340/573.1
See application file for complete search history.

(56) References Cited

U.S. PATENT DOCUMENTS

| | | | | |
|---|---|---|---|---|
| 5,101,828 | A * | 4/1992 | Welkowitz | A61B 5/021 600/481 |
| 10,314,547 | B2 * | 6/2019 | Miller | A61B 5/1495 |
| 2008/0287811 | A1 * | 11/2008 | Nesterov | A61B 5/02405 600/485 |
| 2012/0185195 | A1 * | 7/2012 | Sugiyama | G01N 35/00732 702/85 |
| 2014/0378810 | A1 * | 12/2014 | Davis | G16H 50/70 600/407 |
| 2018/0031669 | A1 * | 2/2018 | Kasper | A61B 5/0507 |
| 2020/0163561 | A1 * | 5/2020 | Choe | A61B 5/02438 |

* cited by examiner

*Primary Examiner* — Omar Casillashernandez
(74) *Attorney, Agent, or Firm* — Amster, Rothstein & Ebenstein LLP

(57) ABSTRACT

A system and method for calibration a system of determining blood pressure based on pulse wave transit time.

11 Claims, 32 Drawing Sheets

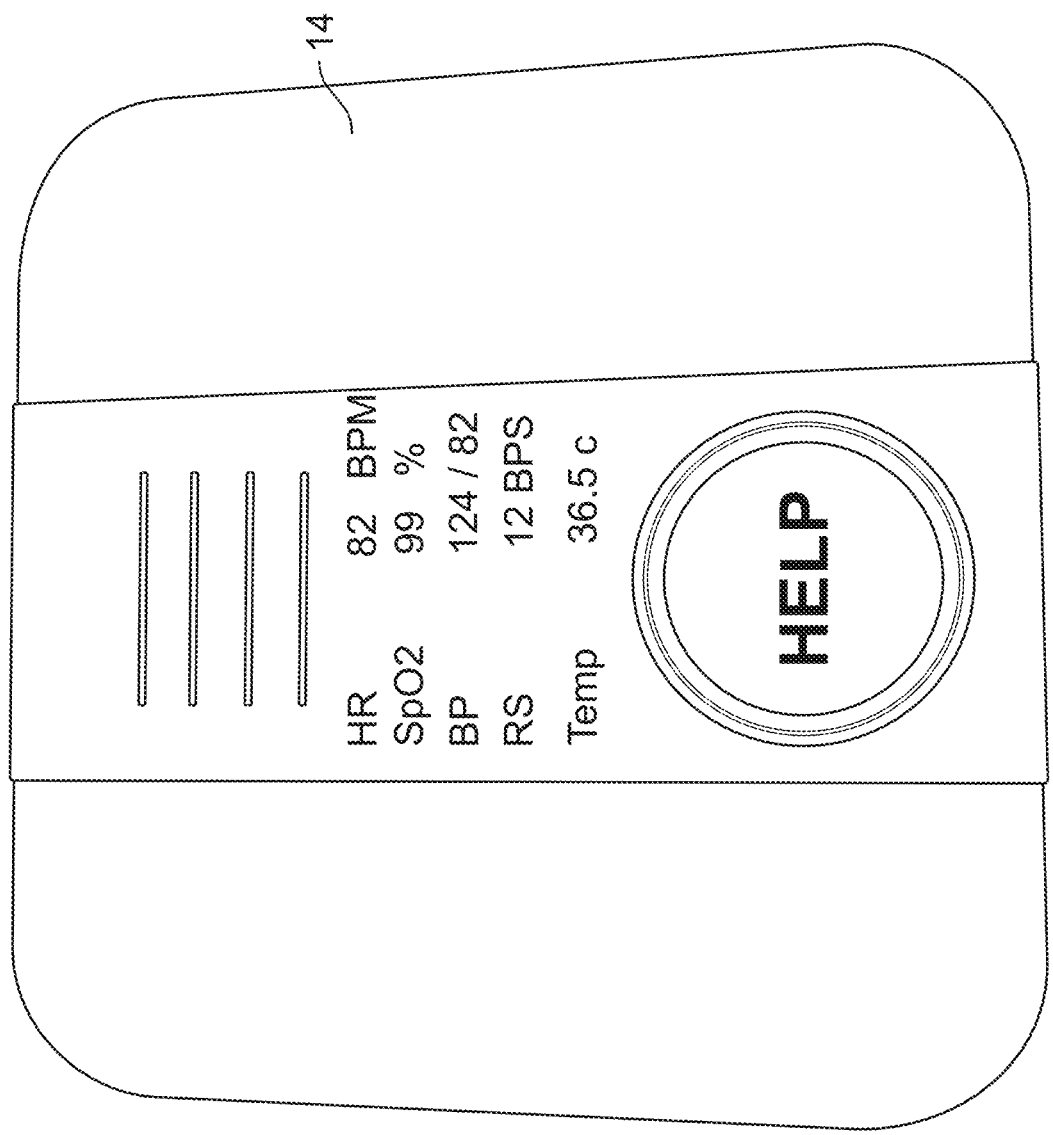

Types

| type | character | examples |
|---|---|---|
| Continued | Does not remit | Typhoid fever, typhus, drug fever, malignant hyperthermia. |
| Intermittent | Temperature falls to normal everyday | Pyogenic infection, lymphoma, military T.B. |
| Remittent | Daily fluctuation >2c, temperature does not return to normal | Not characteristic for any particular disease. |
| Relapsing | Temperature returns to normal for days before rising again | Malaria: tertian-3days pattern, fever peaks every other day (plas. Vivax, plas.ovale), quatrain-4day pattern , fever peaks every third day (p.malaria) lymphomas: HODJKIN lymphoma Pyogenic infection | www.smso.net

FIG. 15

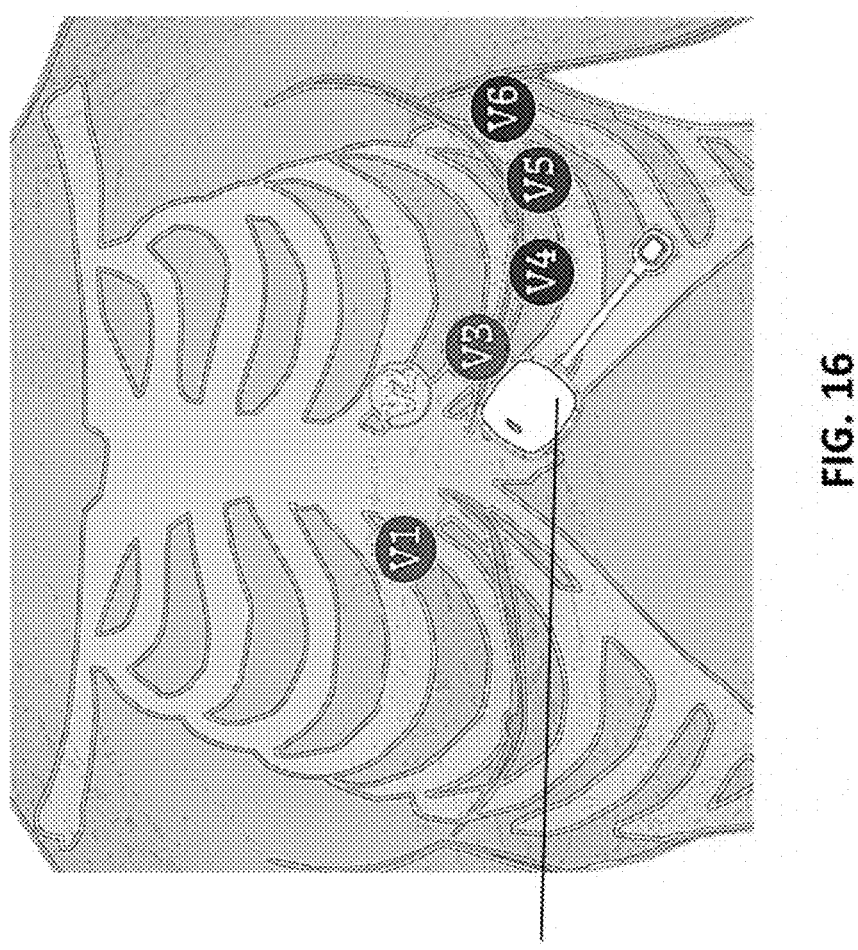

FRONT

BACK

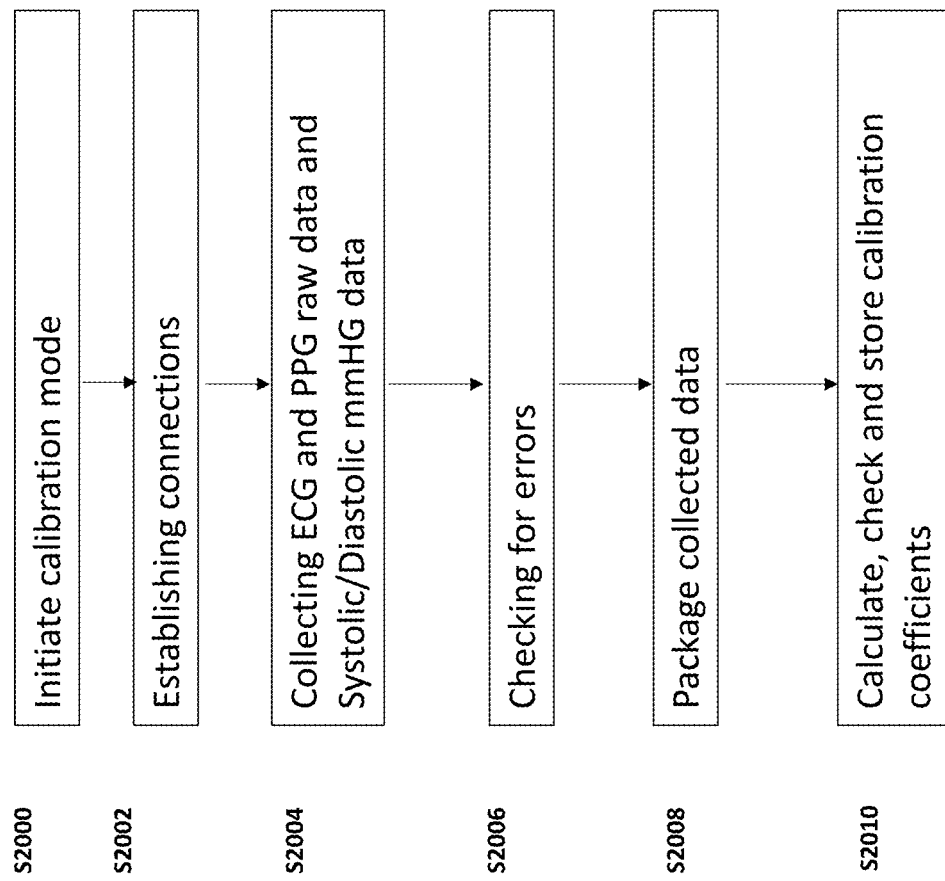

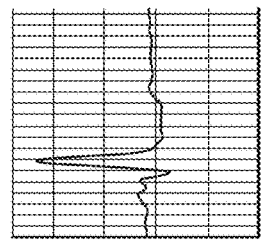 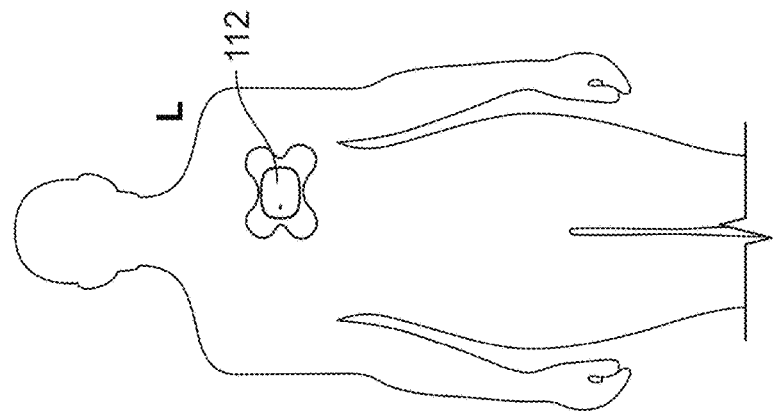
FIG. 28C
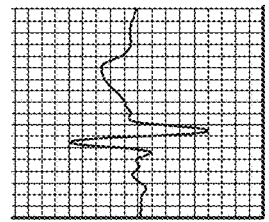 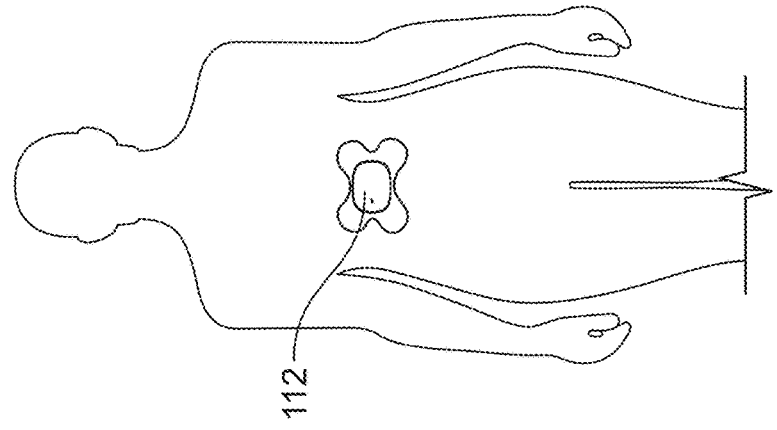
FIG. 28B
 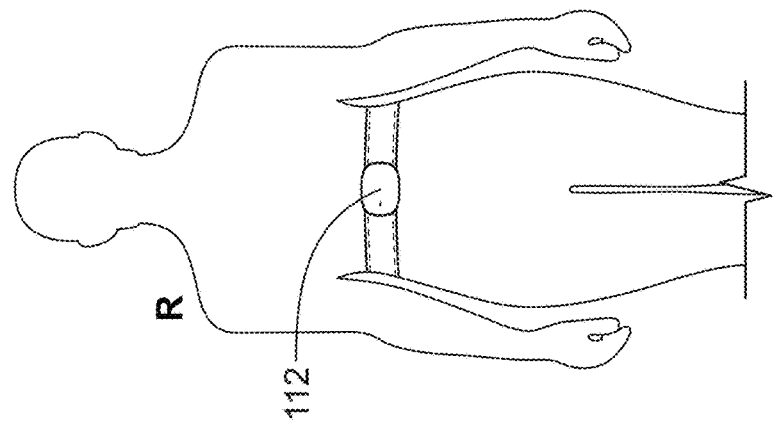
FIG. 28A

SYSTEM AND METHOD FOR CALIBRATING A REMOTE BLOOD PRESSURE SYSTEM

CROSS-REFERENCE TO RELATED APPLICATIONS

The preset application is a continuation-in-part of U.S. patent application Ser. No. 16/356,680 filed Mar. 18, 2019 entitled SYSTEM AND METHOD FOR REMOTE MONITORING OF A USER'S VITAL SIGNS AND BODILY FUNCTIONS which claims benefit of and priority to U.S. Provisional Patent Application Ser. No. 62/643,912 filed Mar. 16, 2018 and entitled SYSTEM AND METHOD FOR REMOTE MONITORING OF A USER'S VITAL SIGNS AND BODILY FUNCTION, the entire content of each of which is hereby incorporated by reference herein.

BACKGROUND

Field of the Disclosure

The present invention relates to a system and method for calibrating a monitoring device to determine a user's vital signs and, in particular, a system and method for calibrating the monitoring device to determine blood pressure based on Pulse Wave Transit Time (PWTT).

Related Art

Healthcare costs have dramatically risen over the last several years. In particular, hospital stays have become more and more expensive making it difficult for patients who require close monitoring such as that available in a hospital setting to afford this type of care. While some such patients can be released to their homes, in order to provide the monitoring they need, it is necessary to provide sometimes equally expensive home healthcare professionals who are physically present in the home. Remote monitoring and access to a user's vital signs may also be useful in other areas, such as athletics.

Blood pressure (BP) refers to the pressure (force per unit area) of circulating blood on the walls of blood vessels. The pressure is generally dependent on work done by the heart pumping blood through the circulatory system. In general, the term "blood pressure" usually refers to the pressure in large arteries of the systemic circulatory system and is usually expressed in terms of the systolic pressure (the maximum during one heartbeat) over diastolic pressure (the minimum pressure between two heartbeats) and is measured in millimeters of mercury (mmHg) relative to atmospheric pressure.

Monitoring blood pressure is important since high blood pressure increases the risk of health problems in the future. High blood pressure puts extra strain on the arteries and on the heart, which, over time strains the arteries and causes them to become thicker and less flexible which may result in weakness. If arteries are thicker and less flexible, they become narrow and make blockage more likely. If an artery becomes completely blocked (known as a clot), this can lead to a heart attack, stroke, kidney disease or dementia. In other cases, if an artery has become weak, the extra strain may eventually lead to the artery bursting. This may also cause a heart attack or stroke.

In addition, low blood pressure may result in dizziness and fainting or may indicate serious heart, endocrine or neurological disorders.

Blood pressure may be measured invasively using an intra-arterial catheter or non-invasively using cuff sphygmomanometer. Use of a cuff is generally less accurate than the arterial catheter, but it is generally more convenient and thus typically used more often. Arterial hypertension is a major problem in modern medicine and health care. Generally, hypertension is defined as a systolic pressure over 140 mmHg and a diastolic pressure over 90 mmHg. Many people suffer from hypertension and are unaware of their condition because of the asymptomatic nature of the disease. In some cases, a patient may have hypertension for 15-25 years without knowing which may result in progressive damage to the cardiovascular system.

Treating and preventing hypertension requires monitoring of blood pressure on a periodic basis. Ambulatory blood pressure monitoring may be used to detect persistently elevated blood pressure during the 2-3 hours after awakening, when the largest proportion of sudden cardiac deaths, myocardial infarctions, and strokes occur.

Commercially available wrist monitors may be used to provide ambulatory blood pressure measurement for people who suffer from hypertension or who otherwise seek to manage their blood pressure. These systems provide for simple operation and allow people to measure blood pressure by themselves regardless of location. Automatic blood pressure measurement systems based on a cuff are pre-programmed to record blood pressure periodically, usually every 15-20 minutes, which may disrupt everyday activities and the loss of important information between measurements. Continuous measurement of blood pressure is important for monitoring blood pressure to prevent hypertension.

Traditionally, blood pressure is measured non-invasively using a combination of auscultation and a mercury-tube sphygmomanometer. The most common automated blood pressure measurement technique is based on the oscillometric method. Both methods require the use of a cuff wrapped around limb of patient. There are disadvantages related to both of these methods. Since blood pressure is affected by a number of factors, such as mood, physiological cycle, physical condition. and the external environment, the results of single or discontinuous measurement may fluctuate greatly. Measurement using a cuff based sphygmomanometer involves human intervention which may introduce mistakes and changes in the patient's physical condition. Measurement using a cuff based sphygmomanometer process is also cumbersome because of the size of the device and the process of attaching it to the patient's body.

In embodiments, blood pressure may be determined based on pulse wave transit time (PWTT) or pulse transit time (PTT). The pulse wave is a wave that precedes blood flow as it flows through the arteries and can be identified using photoplethysmogram (PPG). Thus, monitoring PWTT may be used to monitor patient blood pressure. PWTT, however, is measured in units of time, typically milliseconds. As noted above, conventionally, blood pressure is expressed in terms of systolic and diastolic pressure expressed in millimeters of mercury (mmHG). Thus, PWTT values alone typically do not provide sufficient context to provide useful monitoring for health purposes. Accordingly, it would be useful to provide for conversion of PWTT measurements into systolic/diastolic measurements in mmHG. Further, PWTT measurements may vary depending on the position from which they are measured. Thus, in order to provide effective information, the device used to monitor blood pressure must be periodically calibrated based on the particular position of the device on the particular patient's body.

Accordingly, it would be beneficial to provide a system and method for providing continuous and accurate monitoring of blood pressure including a method for calibrating the system for continuously and accurately monitoring blood pressure.

SUMMARY

It is an object of the present disclosure to provide a method and system to calibrate a system configured to provide comprehensive monitoring of a user's blood pressure.

A method for calibrating a system for determining patient blood pressure in accordance with an embodiment of the present disclosure includes" initiating, by a gateway device, a calibration mode; establishing, by the gateway device, a first connection between the gateway device and a monitoring device mounted on a body of a patient; establishing, by the gateway device, a second connection between the gateway device and a digital sphygmomanometer; receiving, by the gateway device, first collected data from the monitor device, wherein the first collected data includes ECG raw data and PPG raw data; receiving, by the gateway device, second collected data from the digital sphygmomanometer, wherein the second collected data includes systolic/diastolic pressure information indicative of a blood pressure of the patient obtained using a cuff positioned on the patient's body; checking, by the gateway device, the first collected data and the second collected data for errors; packaging, by the gateway device, the first collected data and the second collected data with other data, wherein the other data includes at least a time stamp; calculating, by the gateway device, one or more calibration coefficients based on the first collected data, second collected data and the other data; and storing, by the gateway device, the one or more calibration coefficients in a memory operatively connected to the gateway device.

In embodiments, the step of checking the first collected data and the second collected data for errors includes confirming that a heartrate indicated by the first collected data and second collected data is below a threshold level.

In embodiments, the step of checking the first collected data and the second collected data for errors includes confirming that a heart rhythm indicated by the first collected data and the second collected data corresponds to a normal sinus rhythm.

In embodiments, the time stamp is provided by at least one of the monitor device and the gateway device.

In embodiments, the step of calculating the one or more calibration coefficients further includes: using a first linear equation associated with a systolic pressure number to determine the one or more calibration coefficients; and using a second linear equation associated with a diastolic pressure number to determine the one or more coefficients.

In embodiments, the one or more calibrations coefficients are stored in the memory and are uniquely associated with the patient.

In embodiments, the method includes providing, by the gateway device, a patient record uniquely associated with the patient, wherein the patient record includes the first collected data, the second collected data, the other data and the one or more coefficients; and storing, by the gateway device, the patient record in the memory.

In embodiments, the method includes: providing, by the gateway device, a patient record uniquely associated with the patient, wherein the patient record includes the first collected data, the second collected data, the other information and the one or more calibration coefficients; and storing, by the gateway device, the patient record in the memory.

In embodiments, the patient record includes position information associated with the one or more coefficients, wherein the position information is associated with a position of the monitor device when the first data is collected.

In embodiments, the position information is based on a complex wave signature associated with the first collected data.

In embodiments, the complex wave signature is associated with ECG data provided by the monitor device.

In embodiments, the complex wave signature is associated with a position identifier indicating a specific position of the monitor device.

A method of generating a complex wave signature associated with a position of a monitor device on a patient's body in accordance with an embodiment of the present disclosure includes: receiving, at a gateway device in communication with a monitor device, patient information associated with the patient on which the monitor device is positioned; receiving, at the gateway device, position information indicating a current position of the monitor device on the patient's body; receiving, at the gateway device from the monitor device, ECG data associated with a heartbeat of the patient; determining, by the gateway device, whether the ECG data meets at least one designated criteria; generating, by the gateway device, the complex wave signature based on median values of the ECG data; and storing, by the gateway device, the complex wave signature in at least one memory operably connected to the gateway device.

In embodiments, the patient information is provided via an input device of the gateway device.

In embodiments, the patient information is retrieved from the at least one memory.

In embodiments, the position information is provided via an input device of the gateway device.

In embodiments, the at least one designated criteria is a maximum heartrate.

In embodiments, the at least one designated criteria is confirmation that the ECG data indicates a normal sinus rhythm.

In embodiments, the generating step includes calculating a median for the ECG data provided by the monitor device, wherein the ECG data includes data collected from multiple electrodes of the monitor device positioned at different respective points on the patient's body.

In embodiments, the storing step includes storing the complex wave signature with the patient information and the position information and associating the complex wave signature with the patient information and the position information.

In embodiments, a method of automatically determining a position of a monitor device on a patient's body in accordance with an embodiment of the present disclosure includes: receiving, by a gateway device in communication with the monitor device, a first complex wave signature associated with a first position and a second complex wave signature associated with a second position; receiving, by the gateway device from the monitor device, ECG data associated with a heartbeat of the patient; determining, by the gateway device, whether the ECG data meets at least one designated criteria; generating, by the gateway device, a current complex wave signature based on median values of the ECG data; comparing, by the gateway device, the current complex wave signature to the first complex wave signature and the second complex wave signature; and selecting, by the gateway device, one of the first position and the second position based on a relationship of one of the first complex wave signature and the second complex wave signature to the current complex wave signature.

BRIEF DESCRIPTION OF THE DRAWINGS

The above and related objects, features and advantages of the present disclosure will be more fully understood by reference to the following, detailed description of the preferred, albeit illustrative, embodiment of the present invention when taken in conjunction with the accompanying figures, wherein:

FIG. 6A illustrates another exemplary embodiment of a gateway device used in the system of FIG. 1 in accordance with an embodiment of the present disclosure;

FIG. 15 illustrates a table associating fever patters with diseases;

FIG. 16 illustrates an exemplary placement of the monitor of FIGS. 3A-3C on a user's chest;

FIG. 20 illustrates an exemplary flow chart of a method of calibrating the monitor device to determine blood pressure;

Figure 1:
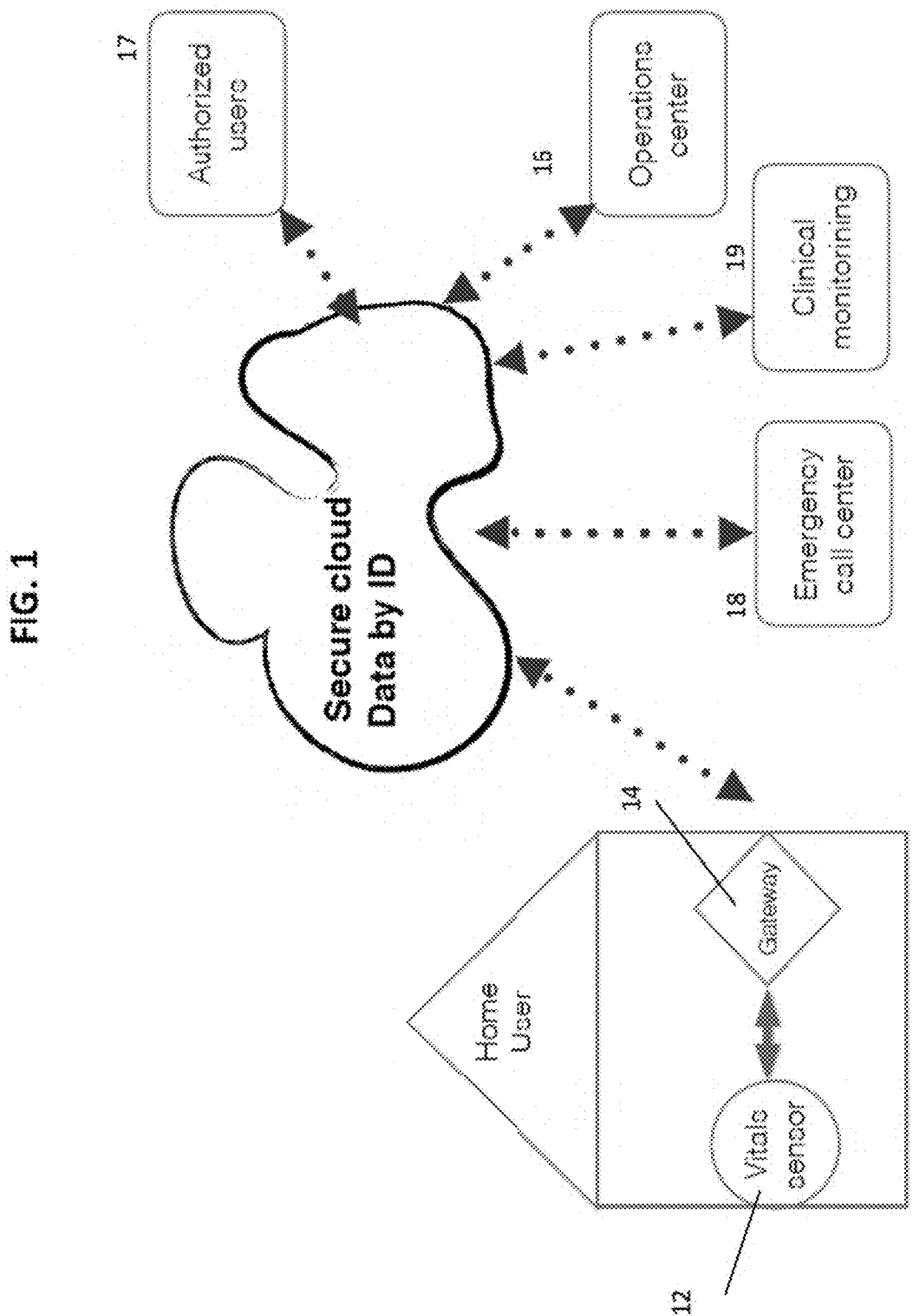
FIG. 1 illustrates an exemplary block diagram illustrating a system for monitoring a user in accordance with an exemplary embodiment of the present disclosure.

27B illustrates an exemplary center of mass of a complex wave signature corresponding to a mid-chest position;

FIGS. 28A-C illustrate exemplary image templates of complex wave signatures and the positions they are associated with.

DETAILED DESCRIPTION OF THE EXEMPLARY EMBODIMENTS

The method and system of the present disclosure relate generally to monitoring user vital signs and other bodily functions for healthcare purposes. In embodiments, vital signs may include, but are not limited to heart rate, temperature, oxygen saturation, respiratory rate and blood pressure, to name a few. More specifically, the present disclosure relates to a system and method for monitoring patient general health and well-being that allows for monitoring, storing and accessing healthcare information remotely. In an embodiment, the system and method of the present application may be used to accelerate a patient's return home from the hospital by allowing medical professionals to remotely monitor the patient while not requiring the patient to stay in the hospital which reduces costs and frees up space in hospitals.

In embodiments, the system and method of the present disclosure may also be used for other applications. For example, in embodiments, the system and method of the present disclosure may be used to allow for remote consultations with doctors or other health professionals without the need for a face to face office visit by providing real-time and historical information regarding the patient's vitals to the doctor or healthcare professional remotely. While the vital information is used herein, the information that is collected and analyzed in the system and method disclosed herein may include other health related information such as activity levels, weight and sleep patterns. Alternatively, in embodiments, the system and method of the present application may be used in an enterprise setting, such as a hospital, nursing home or rehabilitation center to monitor and retain records for a large number of patients.

While the system and method may be used for patients under a physician's care, in embodiments, it may be used in a wide variety of other applications. For example, the ability to remotely monitor a user's vital signs and other bodily functions is may also be useful in athletics. In embodiments, monitoring player vital signs and bodily functions and allowing other parties to access the data allows for players to improve training and performance by allowing coaches, trainers, doctors, etc. to access their body's condition during and after activity. This information may be used to maximize player performance and/or to monitor player health after an injury. In addition, in embodiments, routine monitoring of vital signs and other bodily functions may also be useful for users who are in general good health and are not currently under the care of a physician as a means to maintain good health. In embodiments, routine monitoring of user health may be useful in identifying variations in bodily functions or vital signs that may be an early sign of disease or disorder such that any such problem can be diagnosed or treated early. Early treatment of many diseases or disorders greatly increases the chances of cure and often at the very least, minimizes damage to the body. Thus, the method and system of the present disclosure may be used by a variety of different users in different environments as desired.

In an embodiment, the system 10 of the present disclosure preferably includes a wearable monitor 12 that is in wireless communication with a gateway device or element 14. FIG. 1 illustrates an embodiment in which a single patient or user is monitored in a home setting. In an enterprise setting, in embodiments, multiple gateway devices 14 would preferably be provided throughout a hospital or other institution. In embodiments, multiple monitoring devices or elements 12 may be provided, each one associated with a single patient or user. In embodiments, the multiple gateways 14 may be used to determine a location of a particular patient or user in the facility based. In embodiments, a location of a monitoring device 12, and the patient associated therewith, may be determined by its communication with particular gateway device 14. In embodiments, the gateway device 14 preferably wirelessly communicates with external devices and entities, such as a central monitoring station 16, for example. In embodiments, the gateway device 14 may also communicate with an emergency call center 18. In an embodiment, the gateway device 14 may also communicate with a clinical monitoring center 19. In embodiments, the gateway device 14 sends information to and receives information or instructions from one or more computing device associated with the central monitoring station 16, emergency call center 18 and/or clinical monitoring center 20. In embodiments, the computing device may be any desired computing device, including but not limited to a smart phone including a software application including computer executable instructions to access and view data in the system 10. If desired, other authorized users 17 may communicate with the gateway device 14 as well. These other users may include individual healthcare providers, insurance companies or agents thereof and/or family members of the patient. In embodiments, all communication is bi-directional such that the monitor element 12 and the gateway device 14 transmit and receive information. In an embodiment, communication between the monitor 12 and the gateway 14 is wireless and may use any desired protocol including radio frequency communication as well as optical and/or ultrasonic communication. In a preferred embodiment, the gateway 14 communicates using more than one radio frequency to provide for redundancy to external entities. In embodiments, the gateway 14 may also communicate via wire as well with the central monitoring station 16, emergency call center 18 and clinical monitoring center 19. In embodiments, the gateway 14 may communicate with the central monitoring station 16, emergency call center 18 and clinical monitoring center 19 using any suitable or desired protocol and hardware, including but not limited to PSTN.

In embodiments, the wearable monitor 12 may include a plurality of sensor elements that are used to monitor different patient health functions. In embodiments, the monitor 12 may include a plurality of sensors that gather information sufficient to calculate or otherwise determine information indicative of the user's vital signs and other bodily functions. In embodiments, these calculations may take place in the monitor 12, in the gateway 14 or in any of the central monitoring station 16, emergency call center 18 and clinical monitoring center 19.

Figure 2:
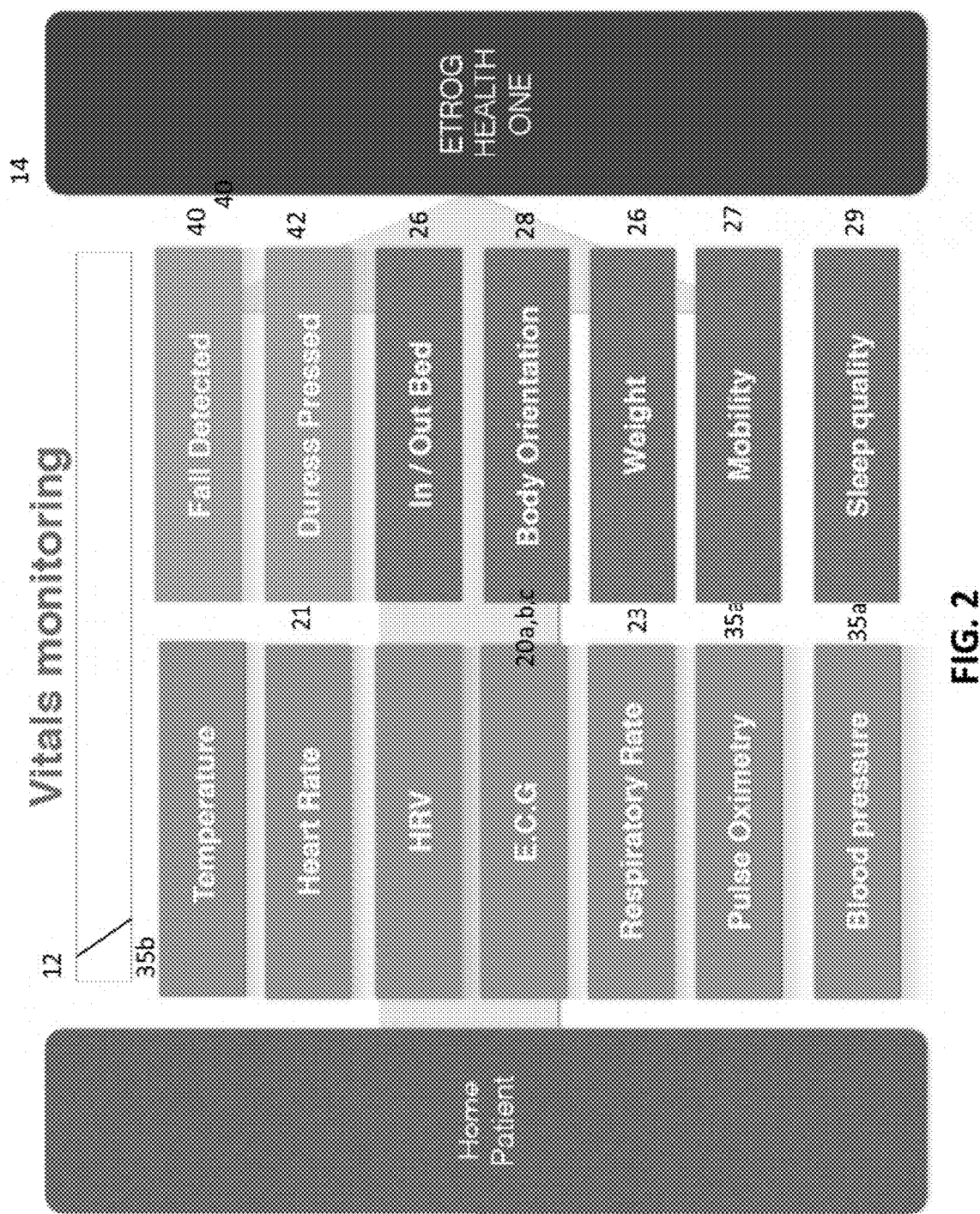
FIG. 2 illustrates a schematic representation of the vital signs and bodily functions of the user monitored in the system of FIG. 1 in accordance with an exemplary embodiment of the present disclosure.

FIG. 2 illustrates the different categories of vital sign and bodily function information that may be provided based on the information gathered by the monitor 12. In embodiments, the wearable monitor 12 may include a temperature sensor 20 to provide an indication of the patient's body temperature. In embodiments, the wearable monitor 12 also preferably includes receptacles 20a, 20b, 20c which are connectable to one or more electrodes E (see FIG. 12, for example) that may be used for an electro cardiogram (ECG). In embodiments, the wearable monitor 12 may also provide blood pressure information 24 as well as a pulse oximetry information 25. In embodiments, mobility information 27 may also be provided as an indication of patient mobility. In embodiments, information regarding orientation 28 may be used to indicate the patient's orientation in bed. In embodiments, sleep quality information 29 may be provided as an indication of the patient's quality of sleep. In embodiments, the sensors used to provide this information are preferably all included in the monitoring device 12 which is connected to the patient.

In embodiments, the system 10 preferable includes other monitors or sensors as well. In embodiments, a scale 26 may be incorporated into the patient's bed to provide an indication of the patient's weight, and provide this information to the gateway 14, either directly or via the wearable monitor 12. In embodiments, the scale 26 may also be used to determine whether the user is in the bed or not. In embodiments, the scale 26 may be embodied as a conventional scale including a wireless transmission element such that it can communicate weight information to gateway 14. In embodiments, a heart rate monitor 21 may be provided to record the patient's heart rate and is preferably provided in the user's bed. In embodiments, a respiratory sensor 23 is also preferably provided in the user's bed and provides an indication of the patient's respiratory rate. These components may be provided separately or integrated together in the in-bed monitoring element 90 discussed below, for example. In embodiments, all of the sensors discussed above provide information about the patient that is keyed to a common time code such that data regarding all parameters of the user's health at a particular time can be linked, recorded, viewed and retrieved.

Figure 10:
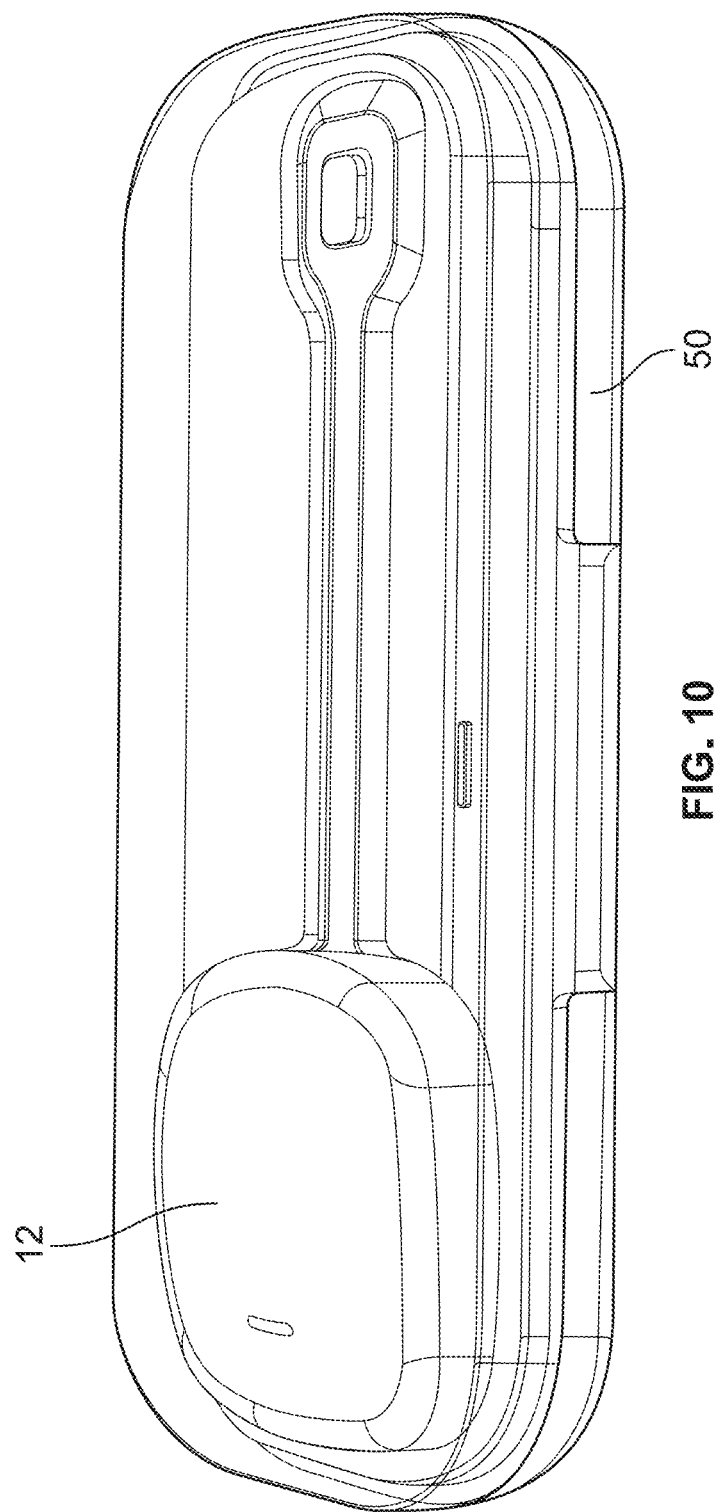
FIG. 10 illustrates an exemplary embodiment of a charging cradle for use in recharging the monitor of FIGS. 3A-3C.

In embodiments, the monitor 12 may be waterproof and is preferably rechargeable. FIG. 10 illustrates an exemplary recharging cradle 50 in which the monitor 12 may be placed for recharging. In embodiments, the recharging cradle 50 may be connected to a power source and also may include a battery such that it can be used to recharge the monitor 12 even in the event of a power failure. In embodiments, the monitor 12 may include charging leads (not shown) for connection to the charging cradle 50. In embodiments, the monitor 12 may include wireless recharging features such that it may be recharged when placed in close proximity to the cradle 50, or simply placed in the cradle 50.

In an embodiment, heart rate, respiratory rate, bed occupancy and sleep monitoring may also be provided by a separate in-bed monitoring element 90. In embodiments, the in-bed monitoring element 90 may be used in addition to the monitor 12 and transmits information to the gateway 14. In embodiments, the in-bed monitoring element 90 is not in contact with the patient's body. In embodiments, the in-bed monitoring element 90 may use ballistocardiography to sense motion changes of the patient which may be used to determine heart rate and respirator rate as well as motion. In embodiments, the monitor 12 may also be used to gather some of the information gathered by the in-bed monitoring element 90, including at least heart rate and respiratory rate information. In embodiments, overlapping information collection may be used to improve accuracy of the monitors 12 and 90 as well as the accuracy of the system 10 as a whole.

Figure 13:
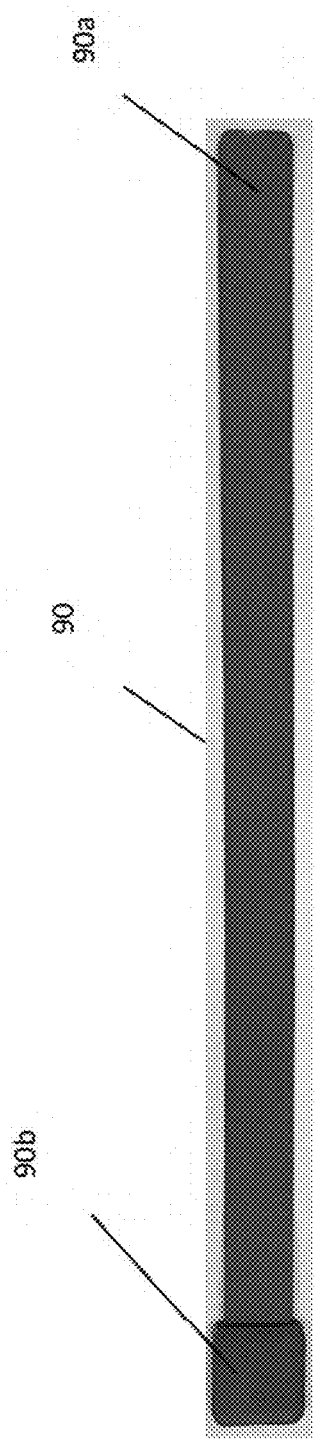
FIG. 13 illustrates an exemplary in-bed monitor suitable for use in the system of FIG. 1.

In embodiments, all of the information gathered, regardless of whether it is gathered by monitor 12 or monitoring element 90, may be time coded such that it may properly correlated when processed to reflect patient health at the same time. FIG. 13 illustrates an exemplary embodiment of the in-bed monitoring element 90 in which the monitoring element includes a sensing portion 90a and a wireless transmitting portion 90b to transmit information to the gateway 14.

In an embodiment, each patient or user may be uniquely identified based on data collected by the wearable monitor 12. In an embodiment, on an initial use, the monitor 12 may gather information about the user's health that is provided to the gateway 14 and used to generate a unique body signature for the individual patient. In embodiments, this signature may be generated by the monitor 12, the gateway 14, or at a central monitoring station 16. In embodiments, the unique body signature may be based on a variety of information gathered by the sensors of the monitor 12 along with other security measures to provide an encrypted signature unique to the user. In embodiments, once this signature is created, it may be stored and each time the monitor 12 is connected to a patient or user, that patient's monitored information will be compared to the unique signature. In embodiments, if there is no match, an alert signal may be provided to indicate that there is a problem or possible fraud. In embodiments, this unique signature may be provided in the calibration step discussed below.

Figure 7:
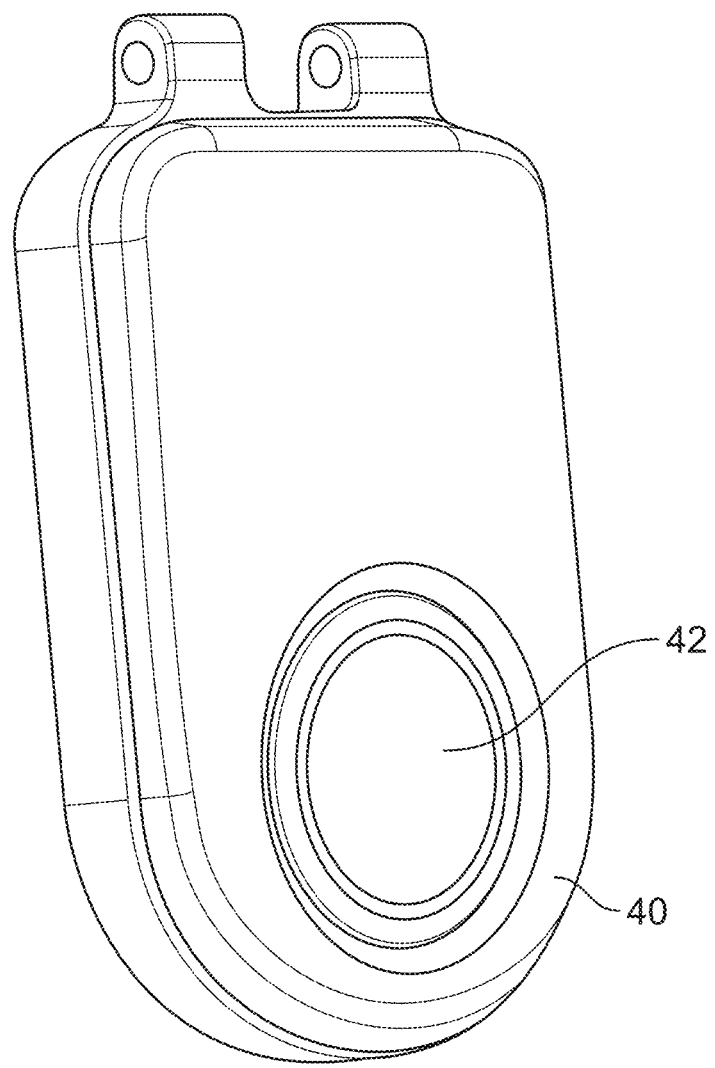
FIG. 7 is an exemplary embodiment of a pendant worn by a user and in communication with the gateway device of the system of FIG. 1 in accordance with an embodiment of the present disclosure.

In an embodiment, the system 10 may also include a pendant device 40 (see FIG. 7), preferably worn around the patient's neck. The pendant device 40, however, may be worn elsewhere or otherwise carried by the patient. In embodiments, while the pendant device 40 should always stay with the user, it should be free to move while on the user. In contrast, in embodiments, the wearable monitor 12 is preferable adhered to the user's skin and stays substantially in the same place while being worn. In an embodiment, the pendant device 40 may include an alert or duress button 42 or other indicator that may be activated by the patient when they are in duress. In embodiments, activation of this indicator transmits a duress signal, or alert signal, which is preferably received by gateway 14, which in turn contacts the emergency call center 18. In embodiments, upon receipt of the duress/alert signal, the call center 18 may provide emergency assistance and/or may contact a health care provider or others to intervene. In embodiments, since communication between the gateway 14 and call center 18 is bidirectional, voice communication may be established between the call center and the patient such that the patient may be interrogated about the cause of distress and a decision may be made about whether intervention is necessary. In embodiments, the call center 18 may provide emergency assistance by contacting local police or fire department to send first responders to aid the patient and/or may contact health care providers in the hospital or home. In embodiments, the call center 18 may also contact the patient's family members or designated emergency contact, if desired. In embodiments the decision and communications discussed above may be made by the central station 16 or the clinical monitoring station 19.

In embodiments, the pendant 40 may include an accelerometer (not shown) which may be used to detect the occurrence of a user fall. In embodiments, in the event of such a fall, the pendant 40 may also transmit the duress/alert signal. In embodiments, the duress/alert signal may be conveyed to the emergency call center 18 as noted above. In an embodiment, the pendant 40 will communicate with the gateway 14 which will then contact the call center 18. In embodiment, the pendant 40 may contact the call center 18 directly. The pendant 40 preferably provided bidirectional communication to the call center 18, either through the gateway 14 or directly, for example, to allow the user to confer with emergency dispatchers and/or medical personnel.

Figure 3A:
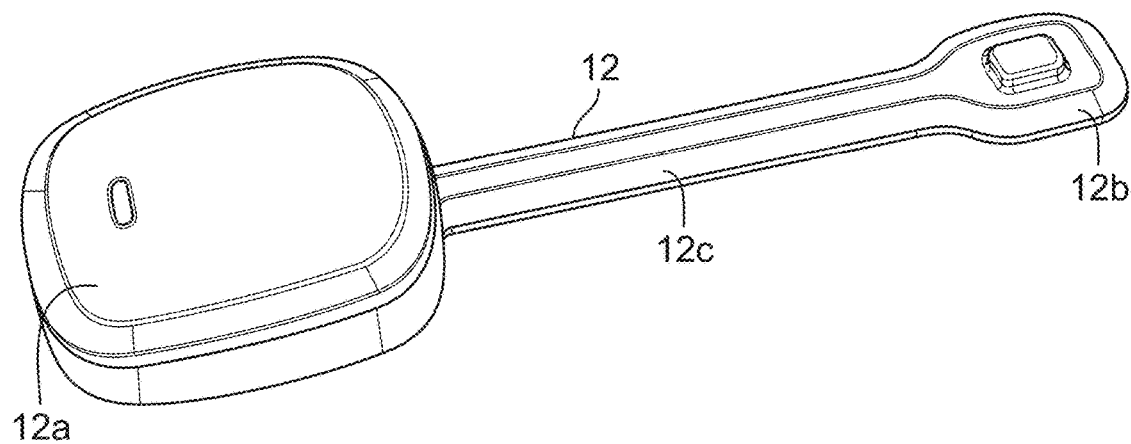
FIGS. 3A, 3B and 3C illustrate an exemplary embodiment of a wearable monitor suitable for use in the system of FIG. 1 in accordance with an exemplary embodiment of the present disclosure.
Figure 3B:
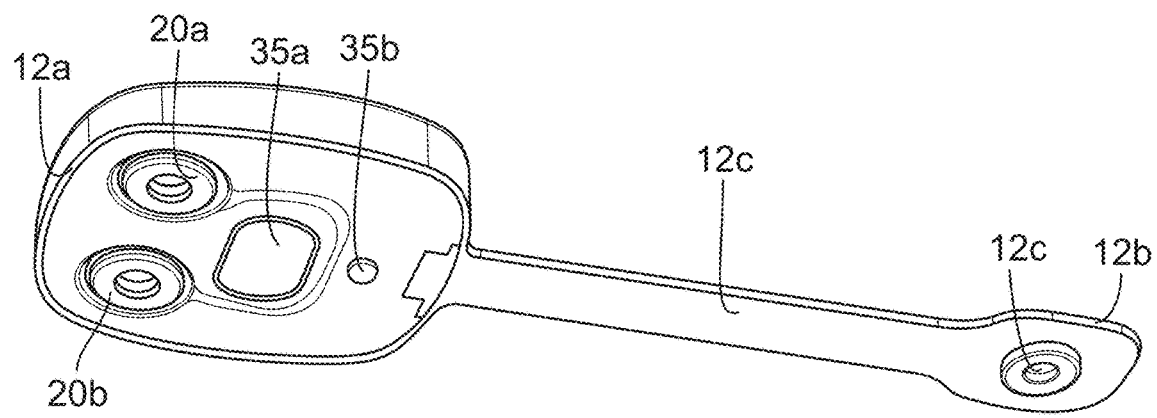
Figure 3C:
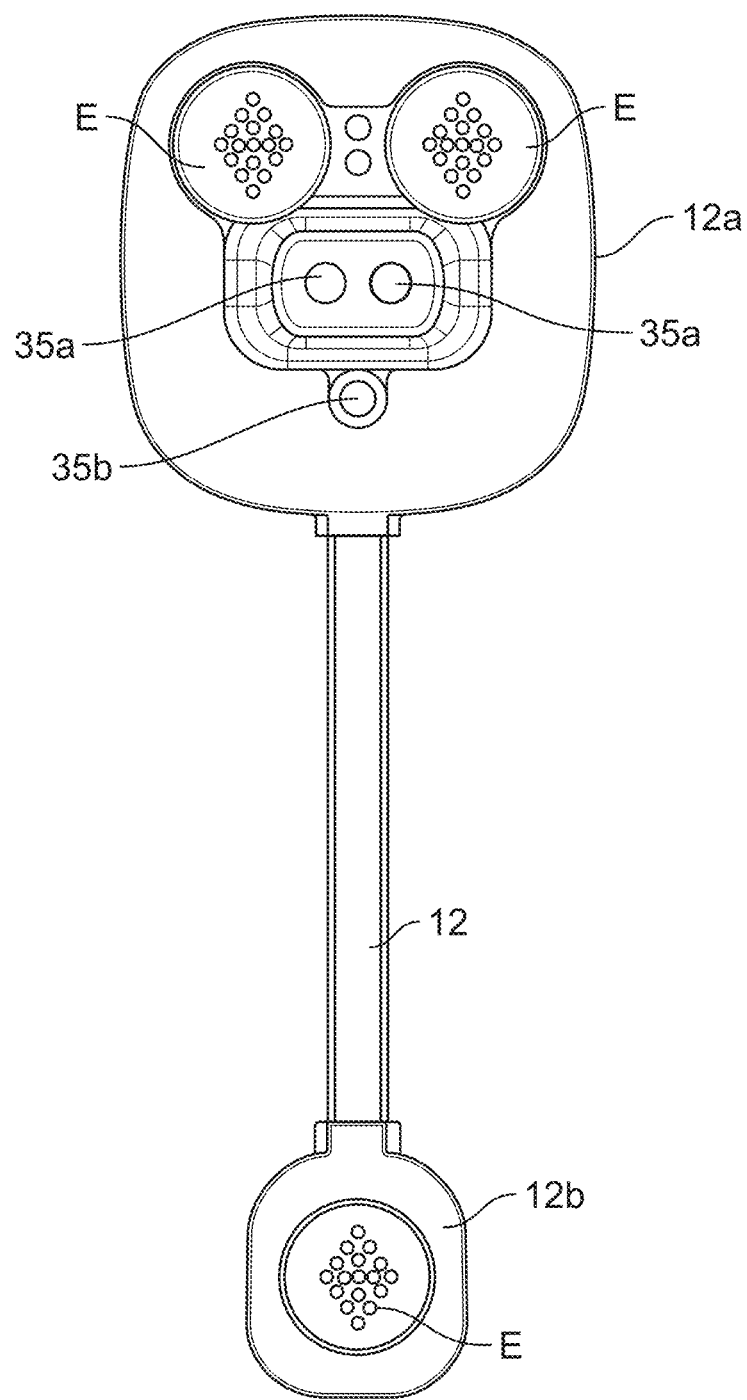

The wearable monitor 12 is illustrated in further detail in FIGS. 3A-3C. In embodiments, the monitor 12 preferably includes electrode receptacles 20a, 20b and 20c (see FIG. 3B) that accommodate electrodes E (see FIG. 3C). In a preferred embodiment, these electrode receptacles are used with "dry electrodes" in that they do not require the use of a conductive gel or other conductive substance to operate. Conventional electrodes such as those used for ECG's are usually "wet electrodes" in that a conductive gel material is applied to the user's skin to ensure good contact and avoid noise during ECG readings. Unfortunately, these conductive gels and other materials are not suitable to remain on the patient's skin for long periods of time since the salts in these materials have a tendency to irritate skin. Since monitor 12 is intended to be worn substantially constantly by a patient for long periods of time, wet electrodes are simply not a good option, although, it is noted that wet electrodes may be used with the monitor 12 as well. In a preferred embodiment, upon application of the monitor 12 to a user's skin, the device performs a test to determine whether the preferred dry electrodes are in use. If not, an alert is issued.

In embodiments, the wearable monitor 12 may be designed to allow for desired positioning of the electrode receptacles 20a, 20b and 20c (and the electrodes positioned therein) to provide accurate ECG results. In addition, the body of the monitor 12 may be designed to provide for relative comfort while providing opportune placement of the electrodes E. In embodiments, the monitor 12 preferably includes a main portion 12a and a smaller secondary portion 12b spaced apart from the main portion on an opposite end thereof. In embodiments, the main portion 12a and secondary portion 12b are connected to each other by a narrow and somewhat flexible bridge portion 12c. In embodiments, as a result, in embodiments, the electrode receptacles 20a, 20b and 20c may be positioned at a desired spacing while the somewhat flexible connection between the main portion 12a and secondary portion 12b allows for comfort as the user moves around during the day. In embodiments, the bridge portion 12c is somewhat flexible and not attached directly to the user's skin which increases comfort for the user such that the main portion 12a and secondary portion 12b are movable with the user's skin while the bridge 12c provides flexibility.

Figure 4:
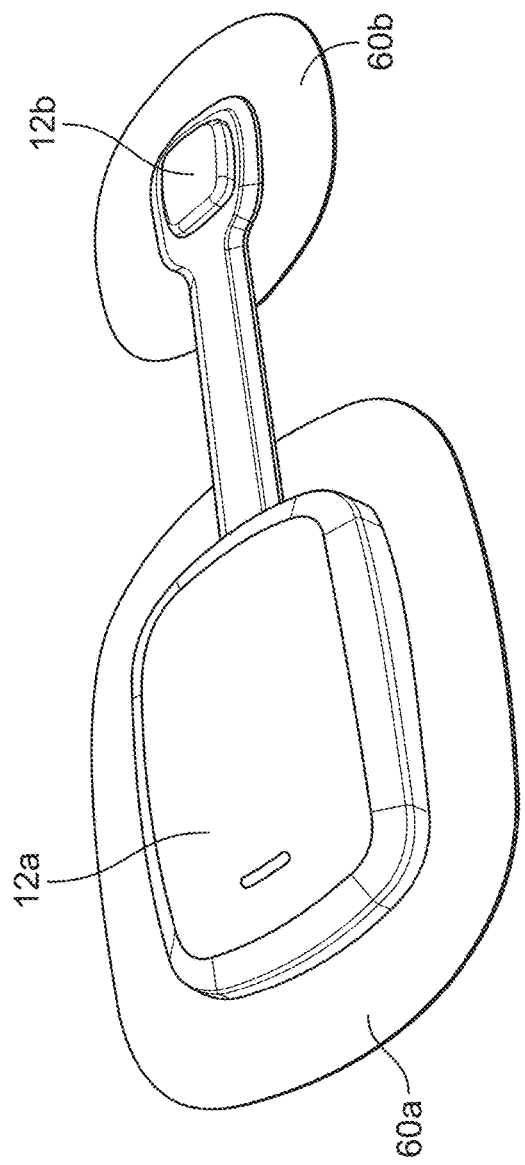
FIG. 4 illustrates the wearable monitor of FIGS. 3A-3C including an adhesive element for adhering the monitor to a patient's skin in accordance with an exemplary embodiment of the present disclosure.
Figure 5A:
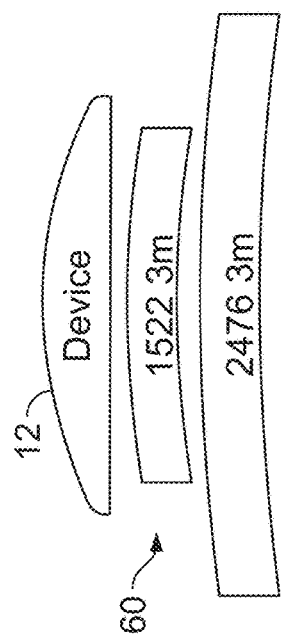
FIG. 5A illustrates an exemplary cross-section of the adhesive element of FIG. 5 connected to the monitor.
Figure 5:
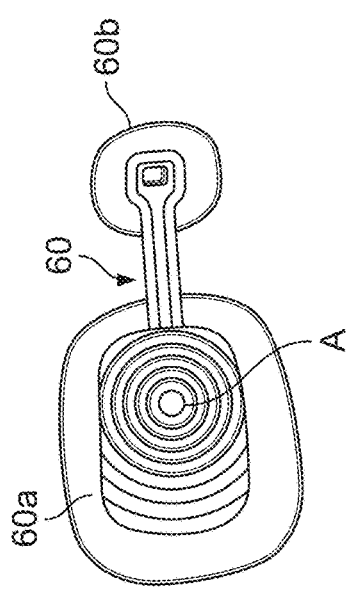
FIG. 5 is a detailed illustration of the adhesive element of FIG. 4 in accordance with an exemplary embodiment of the present disclosure.

The main portion 12a and secondary portion 12b are directly connected to the user's skin via adhesive element 60. In an embodiment, the adhesive element 60 may include a main part 60a and a smaller secondary part 60b. In embodiments, the main part may have an open center region and extends beyond a periphery of the main portion 12a of the monitor 12. In embodiments, the secondary part similarly has an open center portion and extends beyond a periphery of the secondary portion 12b, as can be seen in FIG. 4, for example. In embodiments, the adhesive element 60 preferably includes a lower layer of adhesive that is connected to a user's skin that is hypoallergenic and is preferably made of cloth or silicone, which tend to be less abrasive to skin and add comfort. In embodiments, another adhesive layer may be provided over the lower layer and connects to the monitor 12 which need not be hypoallergenic and may be of any desired material as it does not contact user skin. In embodiments, these multiple layers are visible in the cross-sectional view of FIG. 5A, for example. While FIG. 5A indicates specific products used in the layers, any suitable materials may be used. In embodiments, an applicator A may be provided to guide placement of the adhesive element 60 on the monitoring device 12. While the monitor 12 is preferably adhered to the user's skin, in an embodiment, the monitor 12 may be incorporated into fabric or an article of clothing and held next to the user's body. In such an embodiment, the adhesive element 60 may not be necessary. FIG. 16 illustrates an exemplary positioning of the monitor 12 on a user's chest. FIG. 16 also indicates the various lead placement locations V1, V2 . . . V6 used in conventional ECGs.

Figure 12:
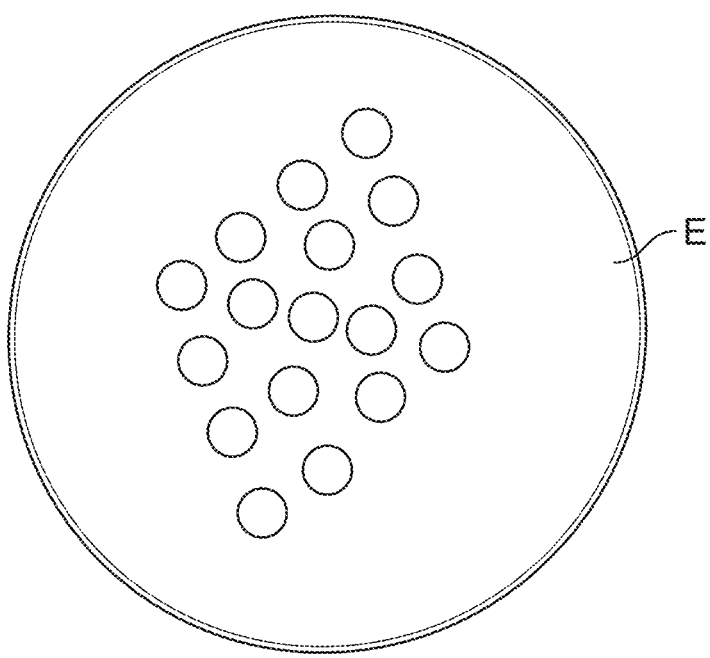
FIG. 12 illustrates an exemplary embodiment of an electrode suitable for use in the system of FIG. 1.

In embodiments, in order to ensure good contact with the user's skin, the receptacles 20a, 20b and 20c are mated with a "dry electrode" as noted above that include a surface with a plurality of raised bumps to contact the user's skin. FIG. 12 illustrates an example of such a dry electrode in which this surface is visible. In embodiments, the receptacles 20a, 20b and 20c, and thus the electrodes E mounted therein, are preferably positioned in alignment with the open portions of the adhesive element 60 such that they can contact the skin of the patient when the monitor 12 is adhered in place on the patient's body. In embodiments, where the monitor 12 is held in place using clothing, an opening may be provided in the clothing to allow the electrodes E in the receptacles 20a, 20b and 20c to contact the user's skin.

In an embodiment, the monitor 12 may include one or more LEDs 35 that are positioned to face the patient when the monitor is in contact with the patient. In a preferred embodiment, a red LED and an infrared LED are included as well as a light meter to detect reflected light from the LEDs. In embodiments, the LEDs 35 and light meter may be used to determine various parameters, including blood pressure, SPO2 and heart rate (pulse). In embodiments, blood pressure estimation may be determined based on pulse transit time (PTT), the interval between the peak of the R-wave in electrocardiogram (ECG) and the peak wave determined by a photoplethysmogram (PPG) sensor measured elsewhere, which is related to arterial stiffness, and can be used to estimate the systolic blood pressure (SBP) and diastolic blood pressure (DBP). In embodiments, the pulse measurement may be obtained based on the use of reflected light from the LEDs. In embodiments, the pulse information in a conventional PTT calculation is gathered at the user's heart and second pulse information is gathered at a finger or other extremity. In the present application, the second pulse location may be in the proximity of the heart and chest as well since the monitor 12 must be positioned in that area to provide an accurate ECG. In embodiments, reflection of light from the LEDs 35a is used to determine pulse at the heart and spaced from the heart. In an embodiment, a modified PTT calculation is provided for estimating blood pressure in view of the close proximity of the two pulse points. In embodiments, this calculation may be performed by the monitor 12, the gateway 14 or elsewhere, such as the central processing location 16 or any other computer system operatively connected to or otherwise connected to one or more of the monitor 12, the gateway 14 or central monitor (processing station) 16. In embodiments, each of the monitor 12, the gateway 14 or central monitor (processing station) 16 include one or more processors that may be used to process data to provide information about the patient's health. Naturally, in embodiments, the LEDs 35a may be used to determine pulse of the patient as well. In addition, in embodiments, a thermistor 35b may be used to determine patient skin temperature.

In embodiments, the LEDs 35a are used as a PPG sensor. In this application, a modified algorithm is also used to allow for patients with darker skin color. PPG sensors use the amount of light reflected such that those with darker skin colors may not reflect sufficient light such that the algorithm is modified to adjust for this.

In embodiments, the system 10 may also be used to determine the location or proximity of a patient. For example, as noted above, in embodiments, in an enterprise environment where multiple gateway devices 14 are positioned throughout a facility, patient proximity and location may be determined based on communication with a particular gateway device. In addition, in embodiments, nurses or other healthcare personnel may carry monitors 12, or variations thereof to track their interaction with particular patients based on their relative position. In embodiments, this may be used in order to ensure compliance with medication and therapy schedules.

In an embodiment, mobility information or proximity information may be used to determine the status of the patient, i.e. resting, walking, running etc. In embodiments, this information may be combined with information on the user's vitals to provide a more useful context for the patient information. For example, an elevated heart rate or blood pressure may not be a cause for alarm if the patient has just walked up a flight of stairs whereas it may be a danger sign if the patient is and has been laying still for some time. Thus, in embodiments, the state of the user is recorded along with the vitals. In embodiments, all of this information is preferably provided to the central monitoring station 16 and preferably to the clinical monitoring station 19. The clinical monitoring station 19 is typically a computing device provided in a hospital or other healthcare facility that analyzes information regarding the patient as would be the case if the patient were in the hospital. In embodiments, where the patient information indicates that the patient may be under duress, an alert may be generated and sent to healthcare providers, family members or emergency contacts. In embodiments, the clinical monitoring station 19 may make decisions based on current information and/or historical information and may also contact the emergency call center 18 to send an alert signal which is acted on as described above. In embodiments, the decisions discussed above may be made by the central station 16 or clinical monitoring station 19.

Figure 6:
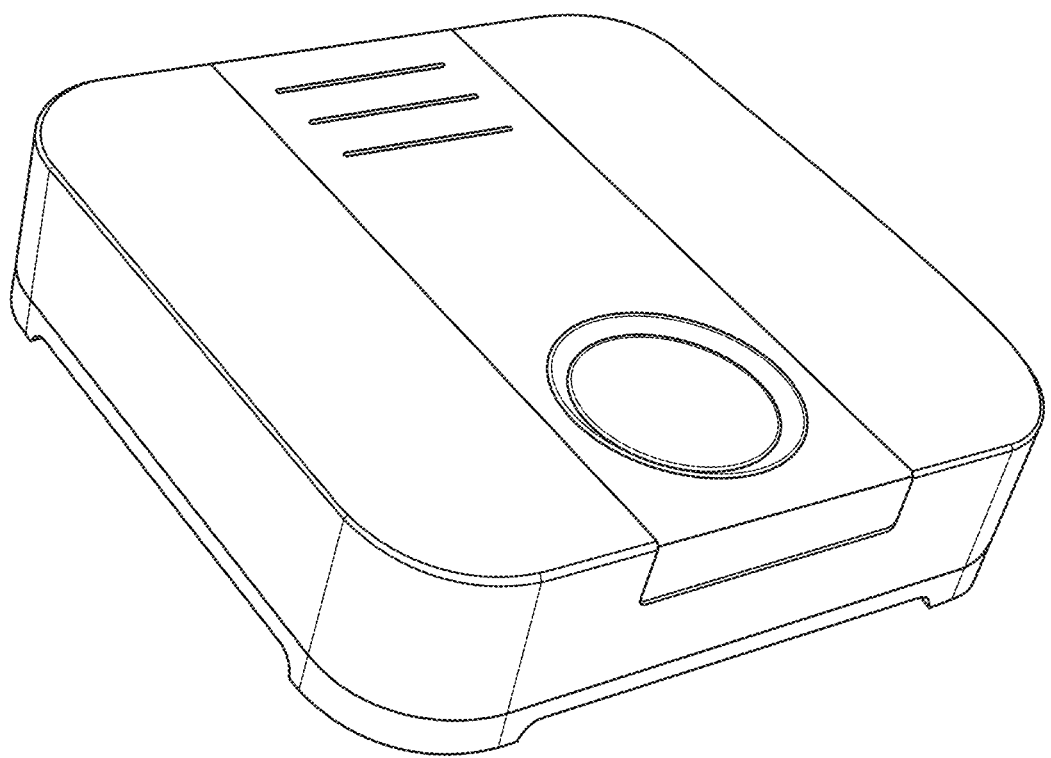
FIG. 6 is an exemplary embodiment of a gateway device used in the system of FIG. 1 in accordance with an embodiment of the present application.

In embodiments, the gateway 14 and monitoring device 12 communicate with each other via bidirectional radio communication such that the device sends data to the gateway and the gateway can send data or instructions to the device 12. In embodiments, the wireless communication between the gateway 14 and monitoring device 12 may be via light or sound, for example, using ultrasonic communication. In an embodiment, the gateway 14 may be programmable with a predetermined test such that a series of measurements may be initiated by pressing a single button or receiving a single command. In embodiment, the single command may be provided by the central station 16, for example. Similarly, in embodiments, the monitor 12 may be preprogrammed in such a manner. In embodiments, the monitor 12 may be programmed to perform desired measurements based on a command received from the central station 16, via the gateway 14. In embodiments, the gateway device 14 also communicates via radio frequency, other wireless communication system or a wired connection with the emergency call center 18, the central monitoring station 16 and clinical monitoring station 19 and allows two way communication such that the gateway can transmit information and can receive information and instructions. The gateway 14 may receive commands regarding taking certain measurement from the central station 16, for example. These commands may be executed by the gateway 14 or passed on to the monitor 12, as appropriate. In embodiments, the bidirectional communication between the gateway and the central station and/or between the gateway and the monitor 12 may be used to update firmware operating in the monitor or the gateway 14. In embodiments, as illustrated, in a preferred embodiment, data may be saved in a cloud setting, however, the data may be saved in any suitable storage element. In embodiments, the gateway 14 may include a display (see FIG. 6A, for example) that illustrates information regarding the user's vital signs or other bodily functions. In embodiments, data that is gathered by the monitor 12 may be checked or verified for errors or corruption before it is transmitted to the gateway 14 and/or the central station 16. If the data is flawed, in embodiments, it will not be transmitted. Similarly, in embodiments, data at the gateway 14 may be checked for errors or corruption before it is transmitted to either the monitor 12 or the central station 16 (or emergency call center 18 or clinical monitoring station 19). In embodiments, flawed data is not transmitted to avoid wasting resources on flawed data.

Figure 8:
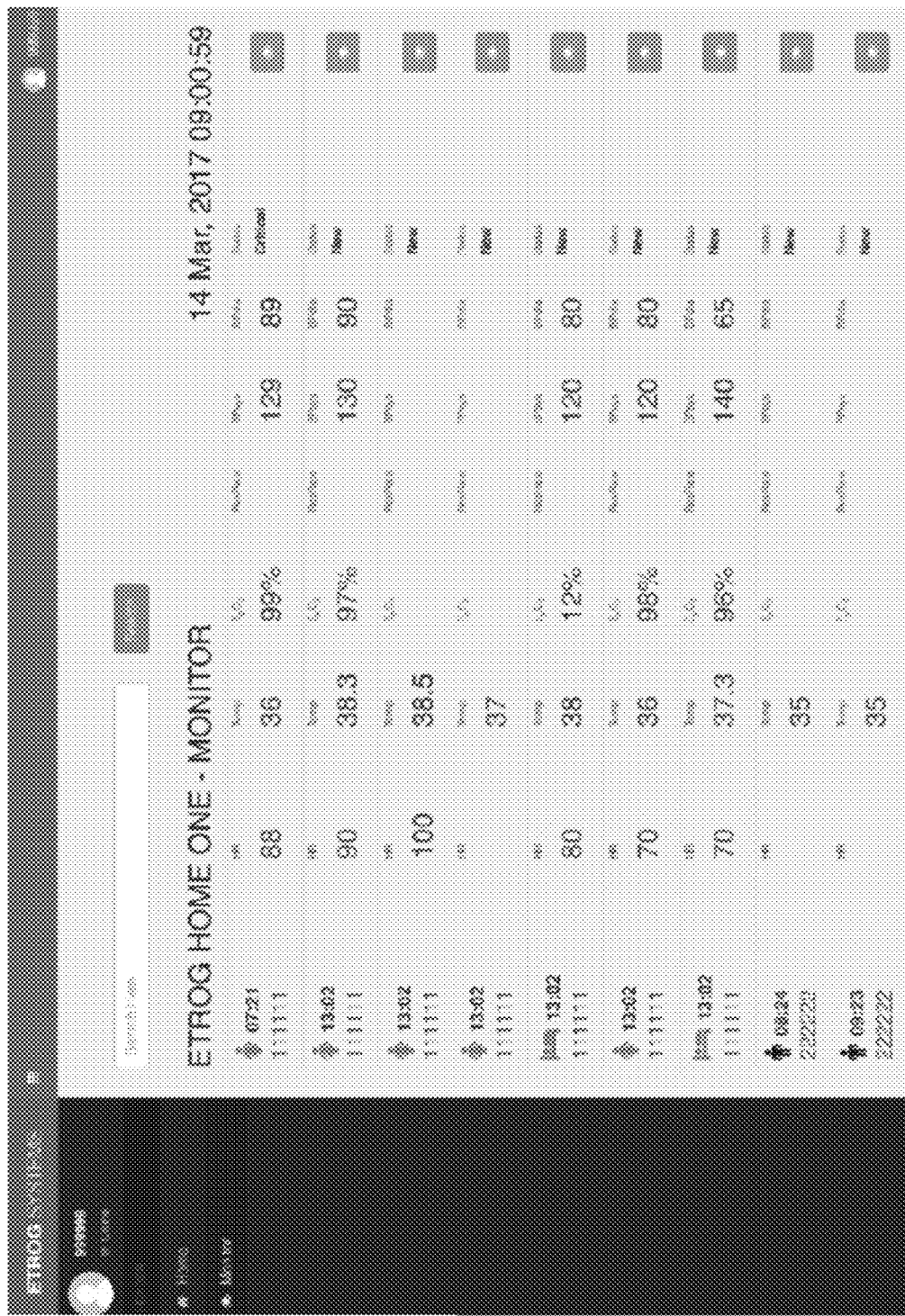
FIG. 8 is an exemplary screen shot illustrating an exemplary graphical user interface for displaying patient information provided by the system of FIG. 1.
Figure 9:
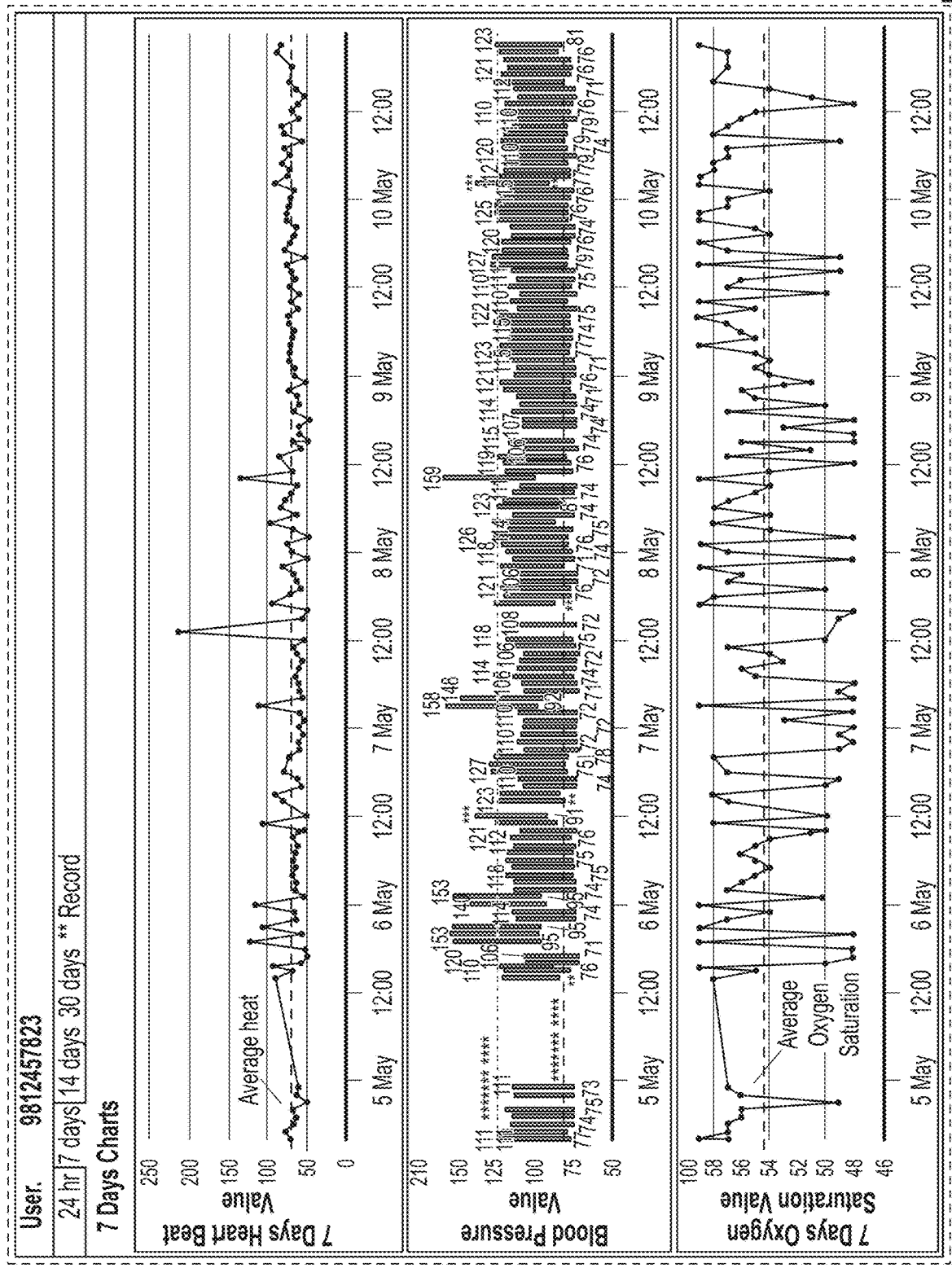
FIG. 9 is an exemplary screen shot illustrating an exemplary graphical user interface for displaying a historical record of certain patient information that was provided by the system of FIG. 1.

In embodiments, the central station 16 may include at least one computing device operably connected to at least one memory element and may store and archive data. In addition, the computing device of the central station 16 includes one or more processors that provide analysis of data including but not limited to the generation of predictive models based on past information for a patient. In embodiments, the data may be viewed by users at the central station 16, at the call center 18 or at the clinical monitoring center 19. In embodiments, the call center 18 and the clinical monitoring center 19 may include one or more computing devices operably connected to one or more memory devices. The computing devices also include one or more processors that may be used to process information received and to allow access thereto. In embodiments, the monitor 12, the gateway 14 and/or central monitor 16 may include one or more processors. In a preferred embodiment, specific users may select the information that they wish to view. In embodiments, information may be viewed in real time, or presented as part of a historical record or both. FIG. 8 illustrates an exemplary screen shot of a graphical user interface usable by a user to view certain patient information. FIG. 9 similarly illustrates an exemplary screen shot of a graphical user interface displaying historical data regarding a patient.

In an embodiment, the information provided by the monitoring device 12 and transmitted by the gateway device 14 is stored and analyzed to provide a vitality score. In embodiments, this may be done at the monitoring device 12, the gateway device 14, the central station 16, the call center 18 and/or the clinical monitoring center 19. In embodiments, the vitality score may generated based on the information regarding vital functions of the patient monitored by the monitoring device 12 with a higher vitality score assigned to patients with desirable results. In embodiments, patient's whose vital functions are observed to be in desirable ranges will be assigned higher vitality scores. In addition, certain functions may be weighted, if desired, to have more or less influence over the vitality score. In embodiments, this calculation is preferably done in the central station 16, but may be done elsewhere in the system 10.

Figure 11:
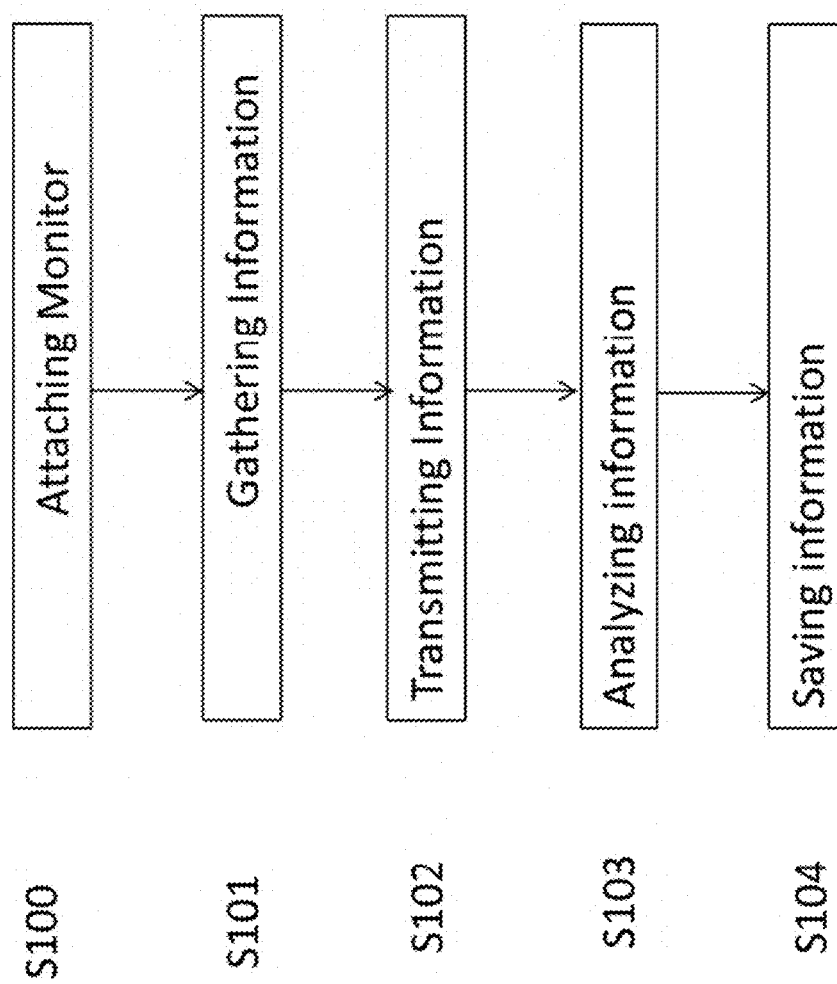
FIG. 11 is a is an exemplary flow chart illustrating a method for monitoring a user in accordance with an embodiment of the present disclosure.

FIG. 11 illustrates an exemplary flow chart for a method of monitoring a patient. In embodiments, in step S100, a monitoring element is attached to the patient's skin. In embodiments, in step S101, the monitoring element may provide information indicating various vital functions and other health related information of the patient. In embodiments, in step S102, the information indicating various vital functions of the patient is transmitted to an external monitoring element. In embodiments, in step S103, the external monitoring element may assess or otherwise analyze the information indicating various vital functions of the patient to determine whether the patient is in distress. In embodiments, this analysis may also take place locally at the monitor 12, gateway 14, central station 16, call center 18 and/or clinical monitoring center 19. In embodiments, if distress is determined, an alert signal may be generated and intervention may be requested. In embodiments, in step S104, the information indicating various vital functions of the patient may be saved in a storage element or any suitable memory element. In embodiments, all of the information may be time stamped such that information regarding different patient functions may be matched to other information from the same time to provide an accurate snapshot of the patient's health at that time.

In embodiments, a calibration step may be provided after step S100 in which the monitoring element 12 and system 10 are calibrated. In embodiments, calibration may be accomplished by comparing measured or calculated values of the system 10 to values that are obtained using so called gold standard devices. In embodiments, the term "gold standard device(s)" generally refers to traditional devices used to measure body function. For example, with respect to blood pressure, a traditional blood pressure cuff is a gold standard device. In an embodiment, the cuff may be automated and provided with a transmission device such that the measured values thereof are transmitted to the monitor 12, gateway device 14, central monitoring center 16 or the clinical monitoring center 19 where they may be recorded and compared to measured or calculated values provided via the monitor 12 or other sensors in order to fine tune the system 10. Alternatively, in embodiments, blood pressure may be manually measured by a healthcare professional with the results may be either transmitted from a personal electronic device or otherwise input by the healthcare provider. In embodiments, another example of a "gold standard device" would be a thermometer for use in determining body temperature. In embodiments, this may be automated in a manner similar to that discussed above with respect to the blood pressure cuff or may be provided by intervention of a healthcare provider. In embodiments, the values measured by such gold standard devices are compared to the measured or calculated values determined by the system 10 to test the accuracy of the system. In embodiments, where there is a discrepancy, the system 10 may be modified to provide for better accuracy and/or the monitor 12 may be repositioned to provide better results. In embodiments, while a blood pressure cuff and thermometer are identified herein as "gold standard devices," it should be understood that there are many other devices that would be considered gold standard devices and this term is not limited to these two examples but includes any devices that are customarily and traditionally relied on by healthcare providers to gather information about patients and their body functions. In embodiments, these devices may be automated, as suggested above, or may be used manually by healthcare providers in order to properly calibrate the system 10. In embodiments, the calibration step discussed above may be repeated periodically, as desired, to maintain accuracy of the system 10. It is noted that the calibration step should always be executed when the monitor 12 is being used in conjunction with a new patient.

In an embodiment, the monitoring element in step S101 is the monitoring element 12 discussed above. In an embodiment, after step S101, the information indicating various vital functions of the patient may be transmitted from the monitoring element 12 to the gateway device 14 discussed above. In embodiments, the gateway device 14 may be used to complete step S102. In embodiments, the external monitoring element may be embodied by any of the central monitoring center 16, the emergency call center 18 or the clinical monitoring center 19 which may process the information indicating various vital functions of the patient as described above. In embodiments, the monitoring element of step S101 may include the in-bed monitoring element 90.

In embodiments, as noted above, one or more LEDs 35*a* on the monitor 12 may be used as a PPG sensor to determine pulse and blood pressure as part of step S101, if desired. Other patient information may be provided via other sensors, such as the thermistor 35*b* and others discussed above.

Figure 14:
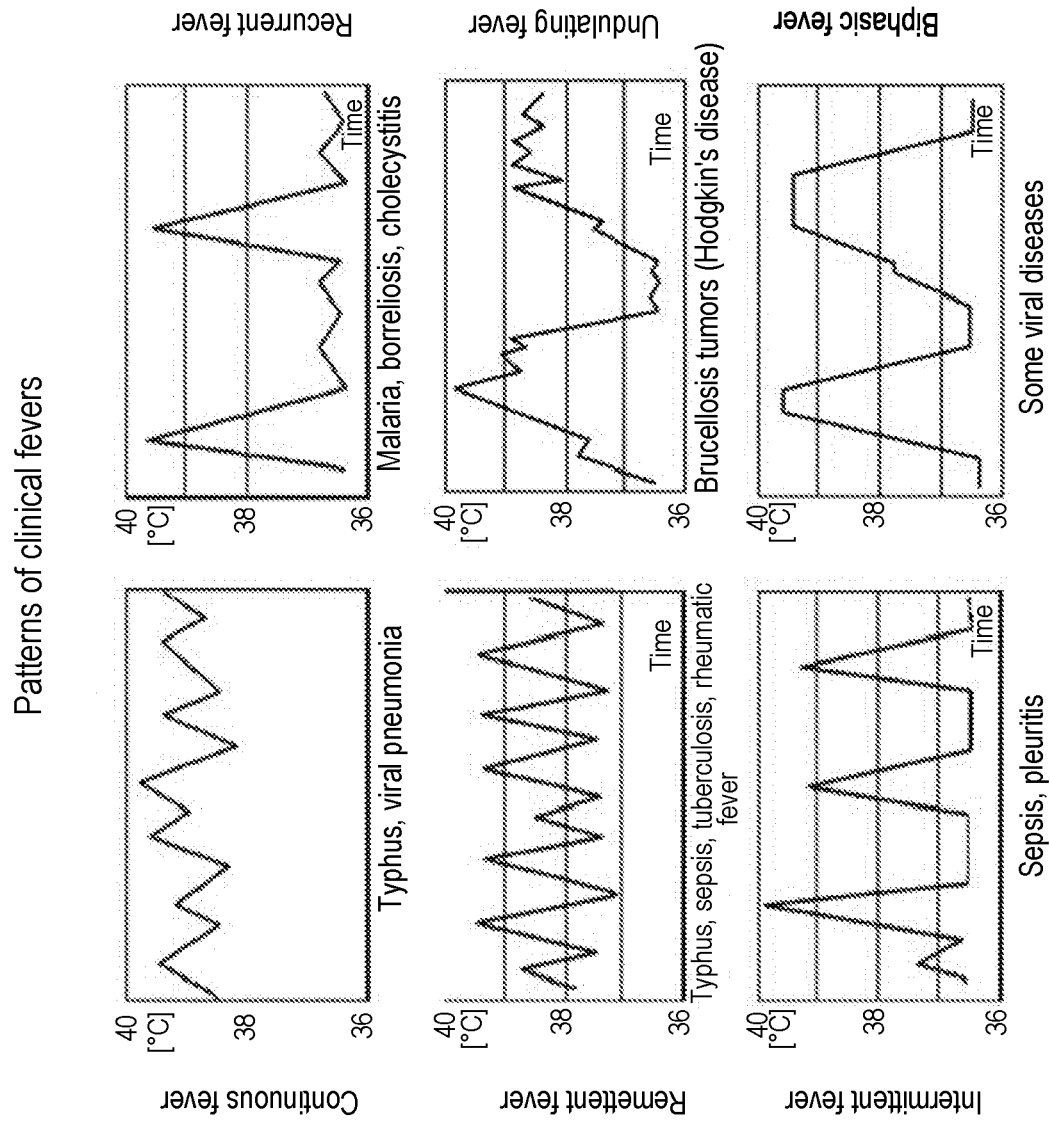
FIG. 14 illustrates a chart illustrating various fever patterns and certain diseases associated with those patterns.

In embodiments, if desired, as noted above, a step of establishing a unique signature of the user may be provided after step S101 or step S102 or as part of the calibration step discussed above. Further, following the storage step of S104, in embodiments, the stored information may be accessed for further processing. In an embodiment, the stored information may be used to make predictive calculations regarding user vitals. For example, past data regarding vital signs may be useful in predicting and diagnosing diseases or disorders. FIG. 14 illustrates various fever patterns and indicates diseases that tend to result in such patterns. FIG. 15 illustrates a table describing some of these patterns and identifying diseases consistent with them. Accordingly, the stored information regarding user vital signs such as body temperature, for example, may be analyzed over a period of time to predict or help diagnose a particular disease of the user. While body temperature is discussed above, patterns may be identified with respect to other patient attributes which may also allow for prediction or diagnosing of disease. In embodiments, the stored information may be used for predicting and diagnosing disease by the central monitor 16, emergency call center 18 or the clinical monitoring center 19.

In addition, the stored information may be used to provide a vitality score, as mentioned above. In embodiments, the vitality score may be used to indicate a general trend in patient health, i.e. improving, degrading or neutral based on the information provided by the system.

The transmitted information may also be analyzed to determine whether intervention is required to aid the user. For example, in the event that the transmitted information includes a duress signal, as discussed above, an additional step of summoning intervention may be added. Alternatively, or in addition, a step of communicating with the user by voice may be added to check on the user's status before summoning intervention. In another embodiment, in the event that the transmitted information indicates that the user is in distress, i.e. dangerously low or high heart rate, blood pressure, pulse, body temperature, lack of mobility for an extended period of time etc., a decision may be made to summon intervention. In embodiments, these decisions may be made at the emergency call center 18, either automatically or based on human intervention, the clinical monitoring center 19 or the central monitoring center 16.

Figure 17A:
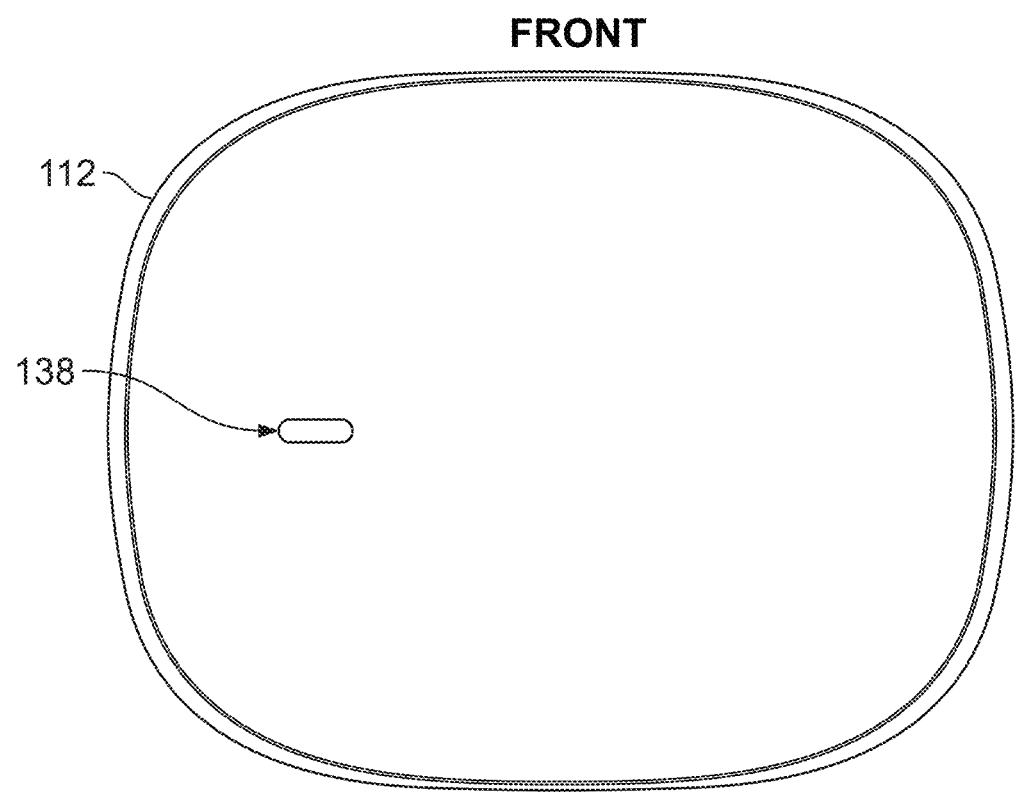
FIG. 17A illustrates a front view of a monitor device used to monitor blood pressure in accordance with an embodiment of the present disclosure.
Figure 17B:
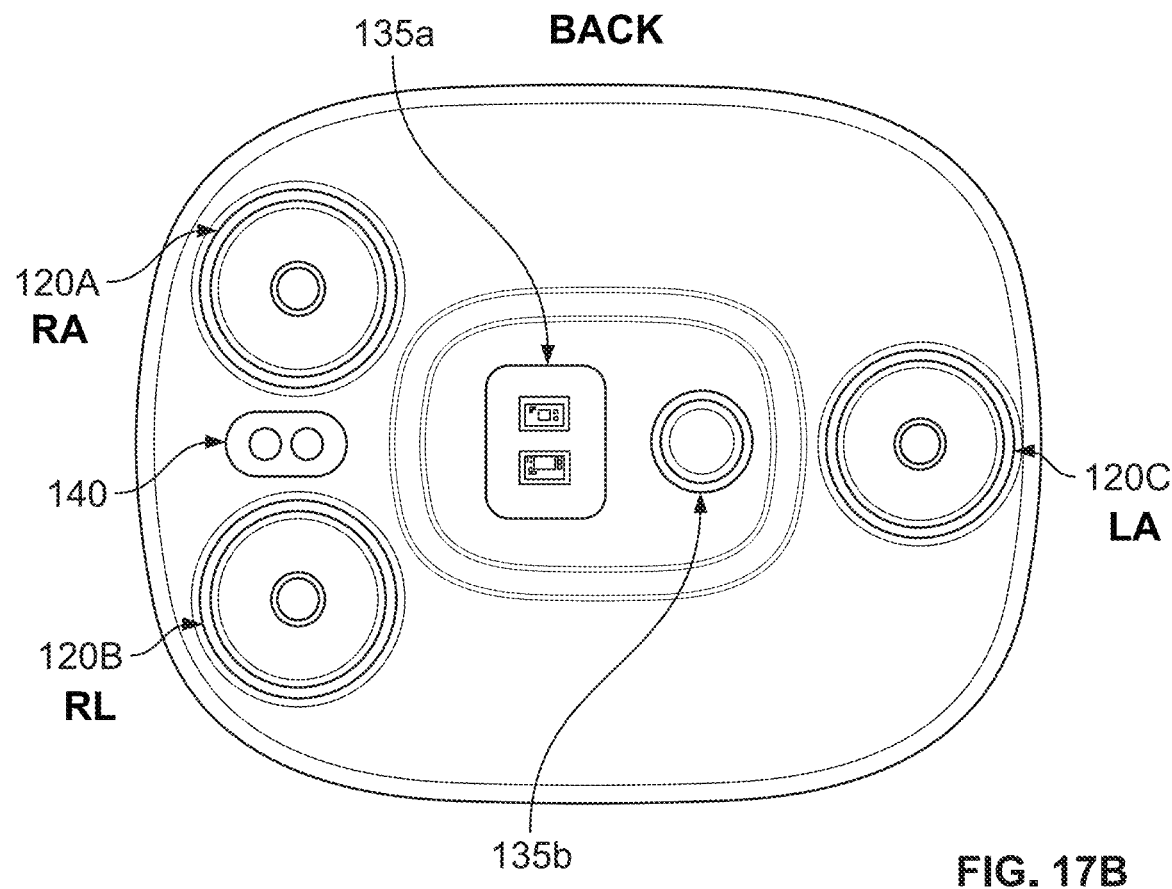
FIG. 17B illustrates a rear view of the monitor device of FIG. 17A.
Figure 17D:
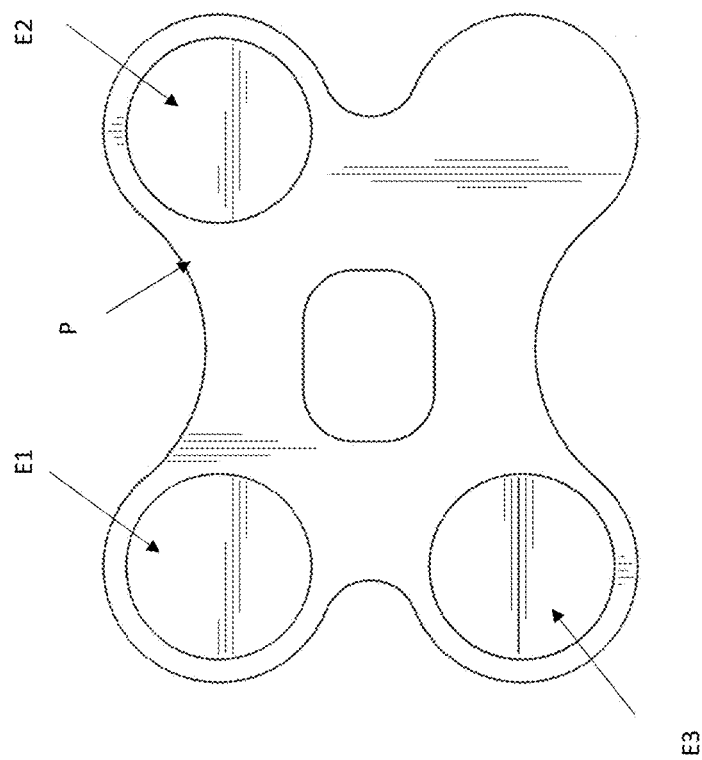
FIG. 17D illustrates a bottom perspective view of a pad or patch to which the monitor device of FIGS. 17A-17B may be attached for mounting the monitor device on a user's body.
Figure 17C:
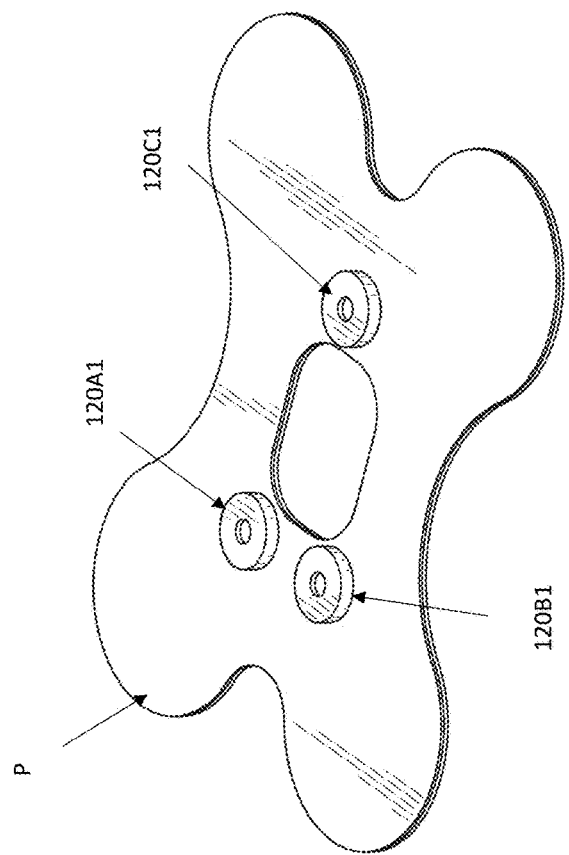
FIG. 17C illustrates a top perspective view of a pad or patch to which the monitor device of FIGS. 17A-17B may be attached for mounting the monitor device on a user's body.

In embodiments, as noted above, a monitoring device 112 (See FIG. 17A-17B) may be used to measure a patient's blood pressure using photoplethysmography (PPG) as well as electrocardiography (ECG). In embodiments, the device 112 may be a wearable device similar to the device 12 discussed above. In the present disclosure, device 12 and the device 112 may be referred to interchangeably. FIG. 17A illustrates an exemplary front view of the monitoring device 112 while FIG. 17B shows a rear, body-facing view thereof. In embodiments, the device 112 may include the electrode receiving portions 120A, 120B, 120C which may be similar to the receiving portions 20A, 20B, 20C discussed above. In embodiments, the receiving portions 120A, 120B and 120C may receive or otherwise be connected to respective electrodes, such as the electrodes E discussed above. In embodiments, the receiving portions 120A, 120B and 120C may be connected to an electrode pad or patch P that may integrate one or more electrodes E1, E2, E3 as can be seen in FIG. 17D. In embodiments, the pad P may include contacts 120A1, 120B1 and 120C1 (see FIG. 17C) that connect the receiving portions 120A, 120B and 120C to the one or more electrodes E1, E2, E3. In embodiments, the monitoring device 112 may include a PPG sensor 135*a*, which may include the LEDs 35*a* discussed above. In embodiments the PPG sensor 135*a* may include additional or fewer LEDs. In embodiments, the PPG sensor 135*a* may be any suitable PPG sensor. In embodiments, the monitor device 112 may include a temperature sensor 135*b*, which may include the thermistor 35b discussed above or any other suitable temperature sensing device. In embodiments, the monitor device 112 may also include one or more charging contacts 140 that may be used to recharge the device 112. In embodiments, the device 112 may be recharged when placed on the recharging cradle 50, or any similar charging cradle or device. As noted above, in embodiments, the monitor device 112 may include wireless recharging circuitry such that recharging may take place when the device is placed near the recharging cradle 50 or other similar device. In embodiments, where wireless charging circuitry is provided, the charging contacts 140 may not be included.

Figure 19A:
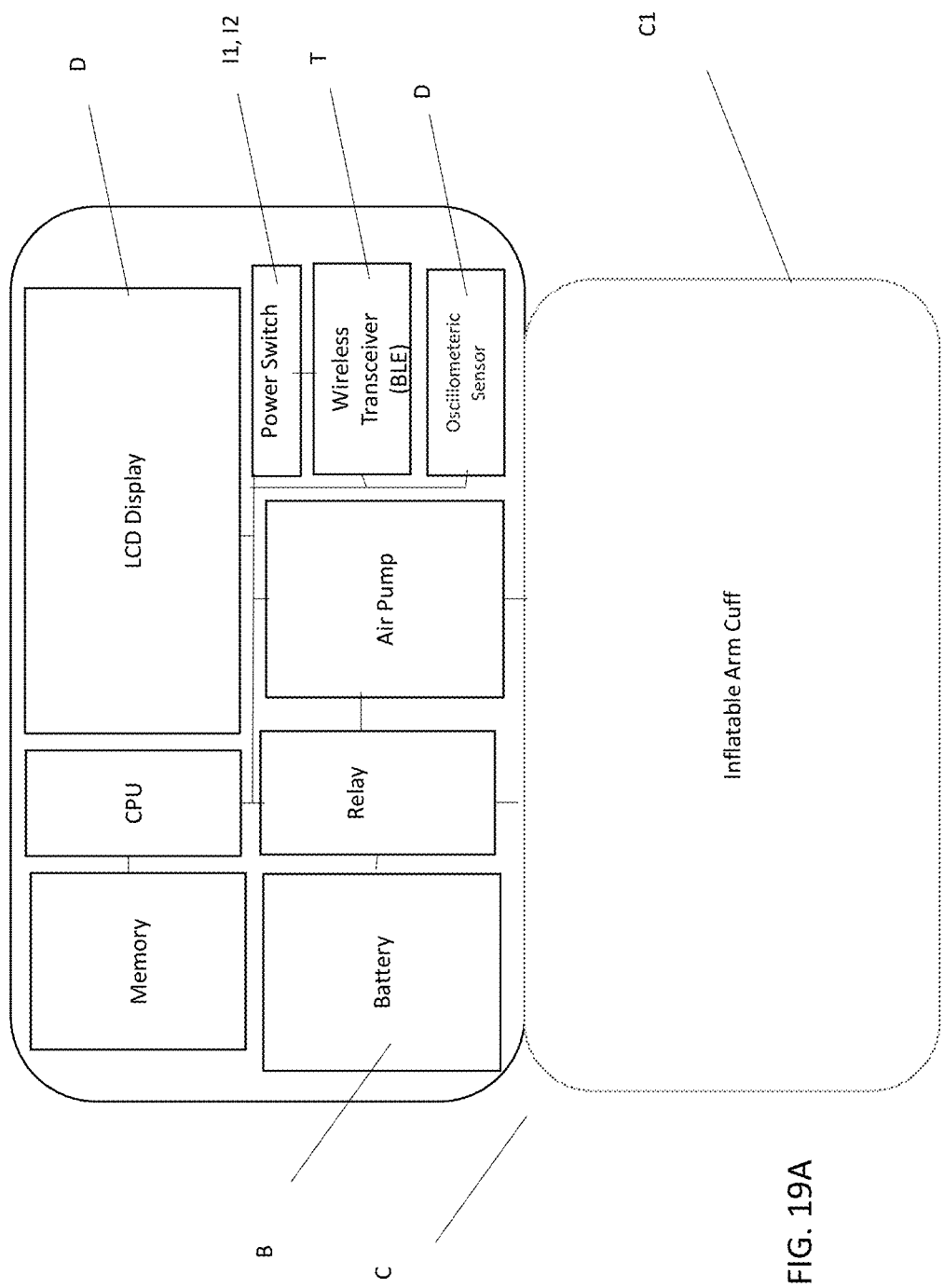
FIG. 19A illustrates an exemplary block diagram of a digital cuff sphygmomanometer.
Figure 19B:
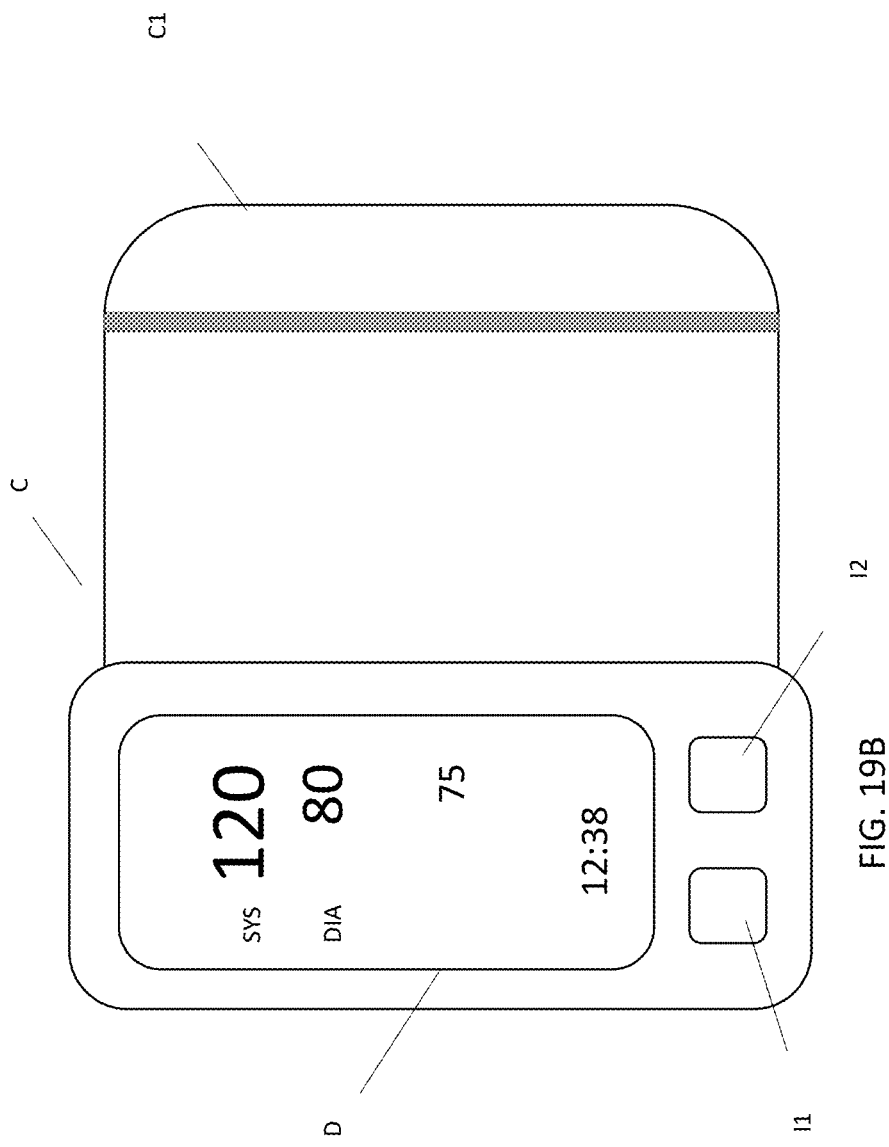
FIG. 19B illustrates a detailed view of an exemplary display of a digital cuff sphygmomanometer.

In embodiments, the monitor device 112 may be used to perform non-invasive blood pressure measurement based on pulse wave transit time (PWTT) (or pulse transit time (PTT) discussed above), as well as other physiological measurements. In embodiments, measurements may be captured continuously without the use of a cuff (such as cuff C of FIG. 19) to provide unobtrusive, handsfree and wireless blood pressure measurement. The use of the monitoring device 112 allows measurements to be performed at remote patient locations without the need for a physician or clinical staff to intervene. In embodiments, the monitoring device 112 may provide continuous measurement throughout each cardiac cycle which is very useful in clinical research.

In embodiments, blood pressure may be determined based on PWTT (or PTT, as noted above) by continuous monitoring of the electrocardiography (ECG) and pulse wave signals resulting from the flow of blood pumped by the heart. In embodiments, PWTT may be calculated for each heart beat based on the ECG data, which is provided based on data provided by the electrodes E1, E2, E3 or electrode pad or patch P, and the resultant peripheral pulse wave which may be detected using the PPG detector 135a.

In embodiments, in order to provide accurate blood pressure measurements using PWTT, periodic calibration of the PWTT measurements with a gold standard blood pressure measuring instrument is important to provide an accurate conversion of PWTT measurements (in milliseconds) to systolic/diastolic pressure numbers expressed in millimeters of mercury (mmHg). Further, PWTT measurements may also vary depending on the individual patient as well as the exact location on the person's body where the PWTT measurements are obtained from such that calibration for each individual patient and each position on the patient is important to provide useful information on blood pressure.

Figure 18C:
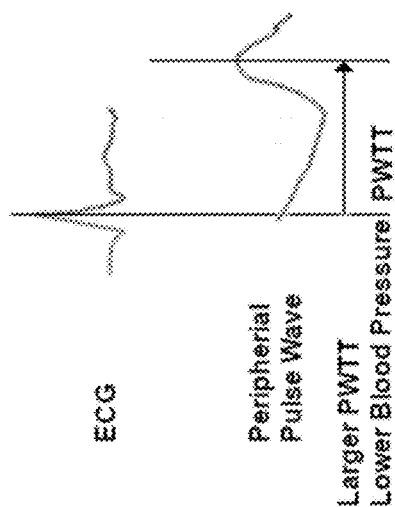
FIG. 18C illustrates an example of ECG data and PPG data indicating a relatively short pulse wave transit time reflecting relatively high blood pressure.
Figure 18B:
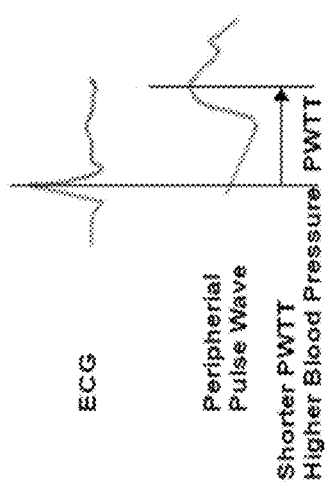
FIG. 18B illustrates an example of ECG data and PPG data indicating a relatively long pulse width transit time reflecting relatively lower blood pressure.
Figure 18A:
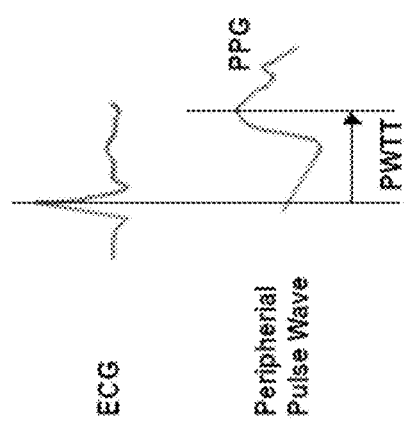
FIG. 18A illustrates the relationship between ECG data, PPG data and pulse wave transit time.

When the heart pumps blood into the aorta, a pressure wave (pulse wave) travels along the arteries ahead of the blood. It is this peripheral pulse wave that is identified based on the raw PPG data to determine, along with the ECG data, a pulse wave transit time in milliseconds. FIG. 18A illustrates the relationship between the ECG, the detected peripheral pulse wave identified based on the PPG data and the PWTT. As noted above, the PWTT is typically expressed in milliseconds. In embodiments, the speed of the pulse wave along the artery is based on the tension of the arterial walls. When blood pressure is high, the arterial walls are rigid and hard such that the pulse wave travels faster, resulting in a short pulse wave transit time as illustrated in FIG. 18B. When blood pressure is lower, the arterial walls are less rigid and the wave travels slower, resulting in a longer pulse wave travel time as indicated in FIG. 18C. That is, the PWTT varies based on the pressure in the arteries, and thus, may be used as an indication of blood pressure in the arteries. In embodiments, detection of the pulse wave, using the PPG sensor 135a relative to the indication on the ECG that the heart has pumped may be used to determine the pulse wave travel time (in milliseconds) as illustrated in FIGS. 18A, 18B and 18C.

In embodiments, the monitor device 112, or the gateway device 14, may initiate a calibration mode to establish the relationship of PWTT (in milliseconds) to systolic/diastolic pressure (in mmHg) for a particular patient. In embodiments, the gateway device 14 may establish a wireless communication link with a gold standard cuff device C (see FIG. 19, for example). In embodiments, the monitor device 112 may establish a wireless communication link with the gateway device 14 as well. In embodiments, the cuff device C and/or monitor device 12, 112 may establish a wireless connection directly with the central station 16 or another server, without involving the gateway device 14. In embodiments, the device 12, 112 may communicate with the cuff device C directly. In embodiments, direct wireless communication links may be established via GSM or another cellular or other wireless network for example. In embodiments, an appropriate FDA approved cuff based digital sphygmomanometer C (see FIGS. 19A-19B, for example) with a wireless communication module, for example, the Biolight Meditech WBP202 with FDA Class II K131558. In embodiments, the digital sphygmomanometer C may include a display D operable to present information to a user, including a blood pressure reading in systolic/diastolic format (in mmHg). In embodiments, the digital sphygmomanometer C may include one or more input elements I1, I2. While the Biolight Meditech WBP202 is specifically discussed herein, other digital sphygmomanometers may be used. In embodiments, one of the input elements I1, I2 may be a power switch to turn the digital sphygmomanometer C on and off, or an activation switch that may be used to trigger a measurement. In embodiments, one of the input elements I1, I2 may be used to provide patient data or health data related to the patient. In embodiments, the digital sphygmomanometer C may include a cuff element C1 that may be attached to a user's arm to obtain blood pressure data. The blood pressure data may be provided to a CPU and may be stored, at least temporarily in the memory. In embodiments, the blood pressure data may be stored for an extended period of time. In embodiments, the blood pressure data may be passed via the relay to the CPU and/or the memory. In embodiments the blood pressure data may be passed via another connection, for example a wire or data bus, to the CPU and/or the memory. In embodiments, a transmitter/receiver (transceiver) T may be included to transmit the blood pressure data or other data, including patient data and/or to receive instructions or other data for operation wirelessly, for example, using Bluetooth or any other suitable wireless communication system or protocol. In embodiments, the digital sphygmomanometer C may include an air pump that may be controlled by the CPU to inflate the cuff element C1 around the user's arm during the measurement process.

In embodiments, the digital sphygmomanometer C may be controlled to take a measurements simultaneously and synchronized with the collection of data by the monitor device 12, 112 via PPG sensor 135a and the electrodes E or the electrodes E1, E2, E3 of the electrode pad. In embodiments, the systolic/diastolic pressure number in mmHG provided by the digital sphygmomanometer C may be associated with corresponding collected data from device 12, 112 based on a time code. In embodiments, the digital sphygmomanometer C may be activated to provide the blood pressure data based on instructions received from the gateway device 14 and synchronized with measurements provided from the monitor device 12, 112. In embodiments, the digital sphygmomanometer C may be activated manually to provide the blood pressure data. In embodiments, the digital sphygmomanometer C may be activated to provide the blood pressure data based on instructions received from the central monitor 16 or another remote server of computer system. In embodiments, the digital sphygmomanometer C may be activated based on instructions received from the monitor device 12, 112. In embodiments, the time code may be provided by the monitor device 12, 112, the gateway device 14 or the central monitor 16. In embodiments, the calculated PWTT, which may be determined based in the data collected by the monitor device 12, 112, and the systolic/diastolic pressure number corresponding thereto may be saved in one or more memories, either included in the device 12, 112, gateway device 14, or central monitor 16 or in a memory operatively connected to one or more of the monitor device 12, 112, the gateway device 14 or the central monitor 16. In embodiments, the associated data may be used to determine a PWTT base line against which specific PWTT measurements may be calculated for a particular user. In embodiments, the base line may be used to determine subsequent PWTT values and corresponding systolic/diastolic pressure number and identify changes that may indicate changes in blood pressure without use of cuff based sphygmomanometer C. In embodiments, the calibration process may include error detection and provide high data accuracy. In embodiments, the monitor 12, 112, the gateway device 14 or central monitor 16 may include one or more processors that may be used to carry out the calibration process.

In embodiments, data collected may be stored in a patient record associated with a particular patient and may include data collected or determined during the calibration process including the baseline. Patient records may be stored in the device 12, 112, in the gateway 14 or in the central monitor 16, and/or in one or more memory elements operatively connected thereto. This data may include:
 (1) test/calibration identification information;
 (2) date/time of start of calibration (Time Stamp);
 (3) systolic/diastolic data (in mmHg);
 (4) Pulse wave travel time data (in milliseconds);
 (5) ECG complex wave signature information;
 (6) Calibrated position information RST;
 (7) Raw ECG wave data;
 (8) Raw PPG wave data;
 (9) User's Body orientation and movement information;
 (10) Skin temperature information.

In embodiments, the test/calibration information may include unique identification information associated with a particular calibration run or cycle. In embodiments, a time stamp, which may include both date and time of the calibration run or cycle may be provided. In embodiments, the time stamp may be or may be included in the unique identification information. In embodiments, the systolic/diastolic data includes an indication of blood pressure in mmHg as determined by the digital sphygmomanometer C, for example. As noted above, the systolic/diastolic data may be transmitted from the digital sphygmomanometer C wirelessly and in coordination with ECG data and PPG data obtained and transmitted by the monitor 12, 112. In embodiments, the raw ECG wave data may be provided by the device 12, 112 using the electrode E or the electrodes E1, E2, E3 of electrode pad P. In embodiments, PPG data may be provided by the monitor 12, 112 based on information provided by the PPG sensor 135*a*. In embodiments, the monitor device 12, 112, or gateway device 14, may include one or more ports or receptacles to allow for wired communication. In embodiments, the raw ECG wave data may include data provided by the electrodes E, or the electrodes E1, E2, E3 of the electrode pads, regarding the electric profile of the patient's heart. In embodiments, the raw PPG wave data may include information associated with the peripheral pulse wave detected in the arteries of the patient by the PPG sensor 135*a* or determined based on data provided by the PPG sensor. In embodiments, the ECG complex wave signature may be used to confirm the position of the monitoring device on the patient. In embodiments, raw ECG data may differ depending on placement of the monitor device 12, 112 on the user's body. In embodiments, an ECG complex wave signature may be determined for each position of the device 12, 112 such that the ECG data may be used to determine or confirm the placement of the device for any successive measurement process. In embodiments, the pulse wave travel time information may be determined based on the raw ECG data and the raw PPG data. As noted above, the pulse wave transit time is a function of the pulse wave as detected by the PPG sensor 135*a* and the ECG data which is based on information provided by the electrodes E or the electrodes E1, E2, E3 of the electrode pad of the monitor device 12, 112.

In embodiments, calibrated position information may include information indicative of a position of the monitor device 112 on the patient's body during the calibration process. As noted above, the calculated PWTT may vary based on position of the monitor device 12, 112 on the user's body. In addition, ECG raw data may vary based on the position of the electrodes E or electrodes E1, E2, E3. In embodiments, calibrated position information includes an indication of a location based on the ECG complex wave signature. In embodiments, this information may be used to determine the position of the device 12, 112 on the user's body such that appropriate baseline information may be used in calculating PWTT. In embodiments, the body orientation information may provide an indication of the orientation of the patient's body as body position may affect measurement. In embodiments, the device 12, 112 may include one or more accelerometers, gyroscopes or other motion detectors that may be used to determine position or posture of the user. In embodiments, the movement information may indicate that the patient has moved or is moving during the calibration cycle. In embodiments, the device 12, 112 may include an accelerometer or other motion sensing device or element that may be used to indicate movement of the user during the calibration cycle. In embodiments, the calibrated position information may be used to provide a location and position of the monitor 12, 112 at the beginning of the calibration process such that movement information provided by the accelerometer or other device may be used to determine whether and how much the user moved during the calibration cycle, In embodiments, some movement of the user during calibration is acceptable, however, in some cases, movement may provide unreliable results. In embodiments, a threshold movement level or amount may be provided or otherwise established and calibration measurements obtained during cycles in which movement exceeds the threshold may be tagged to reflect exceeding the threshold. In embodiments, the calibration cycle may need to be repeated where the threshold is exceeded.

As noted above, the calibration process provides a basis for determining a systolic/diastolic measurement (in mmHG) associated with discrete PWTT measurements (in milliseconds). In embodiments, this determination may be made using two linear equations as follows:

$Y_1=\alpha(\gamma X)|\delta,$ $Y_2=\beta(\gamma X)|\alpha$

The first equation is used to estimate the systolic pressure value (SDP) while the second equation is used to estimate the diastolic pressure value (DBP).

In embodiments, as part of this process, the PPG raw data and ECG raw data are collected using the monitor device 12, 112. In embodiments, the PWTT may be determined based on this information. In embodiments, the calculated PWTT and the measured systolic/diastolic pressure information may be plugged into the first equation as the variables X and $Y_1$ respectively such that the first equation becomes:

$SBP=\alpha(\gamma-PWTT)+\delta.$

In addition, the PWTT and the measured diastolic pressure value DBP are substituted for variables X and $Y_2$, respectively, such that the second equation becomes:

$DBP=\beta(\gamma-PWTT)+\sigma.$

The coefficients α, γ, δ, β ands σ may then be determined. Once these values are determined, these values may be used for future conversions of PWTT to systolic/diastolic pressure information for the same patient where the monitor 12, 112 is in the same position as indicated by the position information. In embodiments, the coefficients may be or may be included in the baseline information discussed above and associated with a particular patient and a particular position of the monitor.

Figure 21:
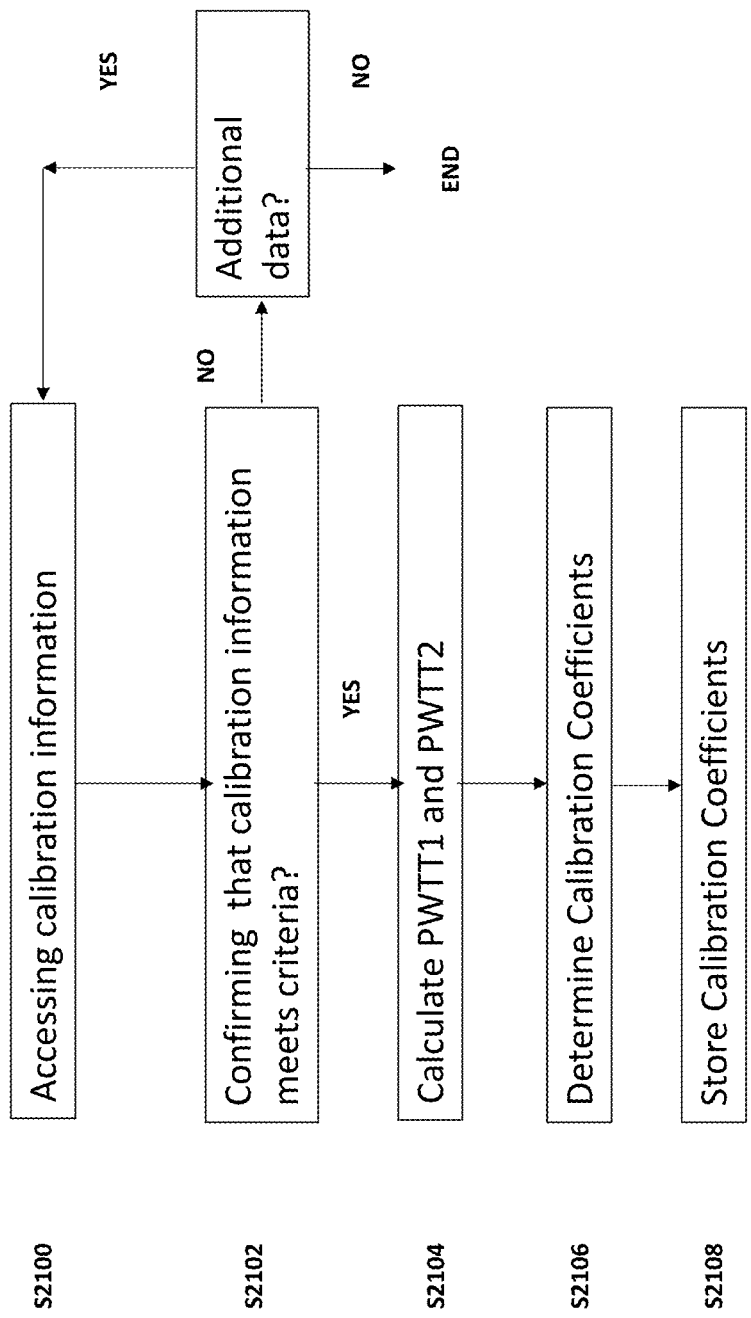
FIG. 21 illustrates an exemplary flow chart of a method of determining coefficients used to convert pulse wave transit time into a corresponding mmHG value(s) indicating blood pressure of the patient.

FIG. 21 illustrates an exemplary flow chart of a method of calculating the coefficients used to determine the systolic/diastolic pressure numbers (SDP, BDP). In step S2100, two sets of calibration measurements, including the ECG raw data and corresponding PPG raw data associated from two different test/calibration runs as indicated by the test test/calibration identification information are provided. In embodiments, this information may be retrieved by the central monitor 16 or by the gateway device 14 or monitor device 12, 112. This information may be retrieved from one or more memory elements included in or operatively connected to the central monitor 16, monitor device 12, 112 or gateway device 14. The retrieved data may be analyzed at step S2102 to determine whether it meets two certain criteria. In embodiments, a first predetermined criteria is that the test runs must be dated within a predetermined time period. In embodiments, the predetermined time period may be 30 days. In embodiments, the predetermined time period may be longer or shorter than 30 days. In embodiments, a second predetermined criteria may require that there be a difference of at least 15 mmHG in the systolic/diastolic measurement value between each test run. If both criteria are met, at step S2104, a first pulse wave travel time (PWTT1) is calculated for the first test set and a second pulse wave travel time (PWTT2) is calculated for the second test set. Otherwise, at step S2102a determination is made as to whether another set of test data is available. If so, the other set of data is retrieved and step S2102 may be repeated. If not, the method may terminate.

After the PWTT1 and PWTT2 are determined, in step S2104, the coefficients α, γ, δ, β and σ may be calculated in step S2106. In embodiments, the coefficients may be determined based on the following equations:

$$\alpha = \frac{(SBP1-SBP2)}{(PWTT2-PWTT1)}$$

-continued $$\beta = \frac{(DBP1-DBP2)}{(PWTT2-PWTT1)}$$

$\delta = SBP2$ $\sigma = DBP2$ $\gamma = PWTT2$

Thereafter, the calculated coefficients may be saved in a memory included in or operatively connect to the device 12, 112, the gateway device 14 or the central monitor 16 in step S2108. In embodiments, the method of FIG. 21 may be implemented in any one of the devices 12, 112, the gateway device 14 or the central monitor 16. In embodiments, the gateway device 14 may be a smart phone, tablet or other mobile electronic device. In embodiments, the gateway device may be a laptop computer, personal computer or any other computer system. In embodiments, the method of FIG. 21 may be implemented in another server or computer system in communication with any of the devices 12, 112, the gateway device 14 or the central monitor 16. After storage, the coefficients may be used in the future to determine systolic (SBP) and diastolic (DBP) pressure values for the patient based on the raw ECG and raw PPG data provided by the device 12, 112 in accordance with the equations discussed above.

In embodiments, error detection may be included in the calibration process. In embodiments, where a measurement fails to meet a threshold, this may indicate an error and initiate a re-test or re-calibration. In embodiments, where the ECG data indicates a heartrate over 120, this may indicate an error in the collected information, In embodiments, where the ECG data indicates an irregular heartrate (i.e. non-sinus rhythm), this may be an indication of an error. In embodiments, in the event of detection of an error, the calibration process may need to be repeated. In embodiments, where an error is detected, the calibration process may terminate. In embodiments, where an error is indicated, the calibration process may continue and an error tag or notice may be included in or associated with any data that is collected. In embodiments, the criteria discussed above may be used in error detection.

Figure 23:
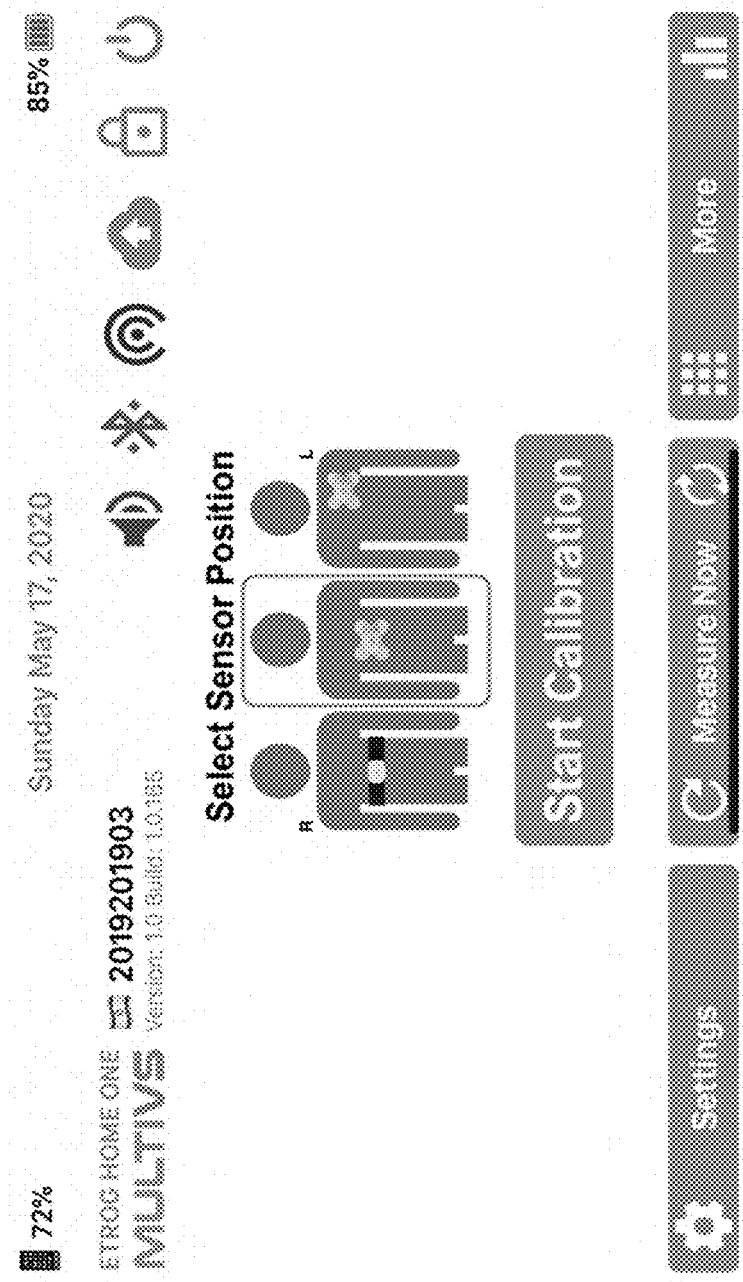
FIG. 23 illustrates a screenshot showing exemplary placements of the monitor device of FIGS. 17A and 17B on a patient's body that may be selected.

In embodiments, a position of the monitor device 12, 112 may be determined automatically. In embodiments, the monitor device 12, 112 may be placed in different positions, for example, the mid chest or the left chest. FIG. 23 illustrates three exemplary positions for the monitor device 12, 112. Different positioning of the monitor device 12, 112 may result in a difference in the collected data and the calculated PWTT data and/or the signals read. Further, since the device 12, 112 is configured to implement remote patient monitoring, the positioning of the device 112 is not supervised by a doctor or other medical professional. In embodiments, therefore, measurements taken by the device 12, 112 may be correlated with the position of the device during the measurement. In embodiments, the ECG measurements, i.e. the ECG raw data, may be analyzed to determine the position of the monitor device 12, 112 based on an ECG complex wave signature that may be stored as noted above. In embodiments, the wave signature may be used during regular operation, that is, after calibration has been completed and the device 12, 112 is being used to continuously monitor blood pressure to determine or confirm the current position of the monitor device 12, 112 such that appropriate coefficients are used to determine blood pressure based on PWTT. In embodiments, the signature may be used to confirm that the monitor device 12, 112 is in the same position as it was during calibration. If the monitor device 12, 112 is not located in a known position, the proper calibration coefficients may not be used and the systolic pressure number SBP and/or diastolic pressure number DBP determined based on the PWTT may be incorrect. If no position for the monitor device 12, 112 is determined, an alert may be provided in the analysis result presented to a physician or other health care professional. As a result, the accuracy of the presented report may be improved.

Figure 22:
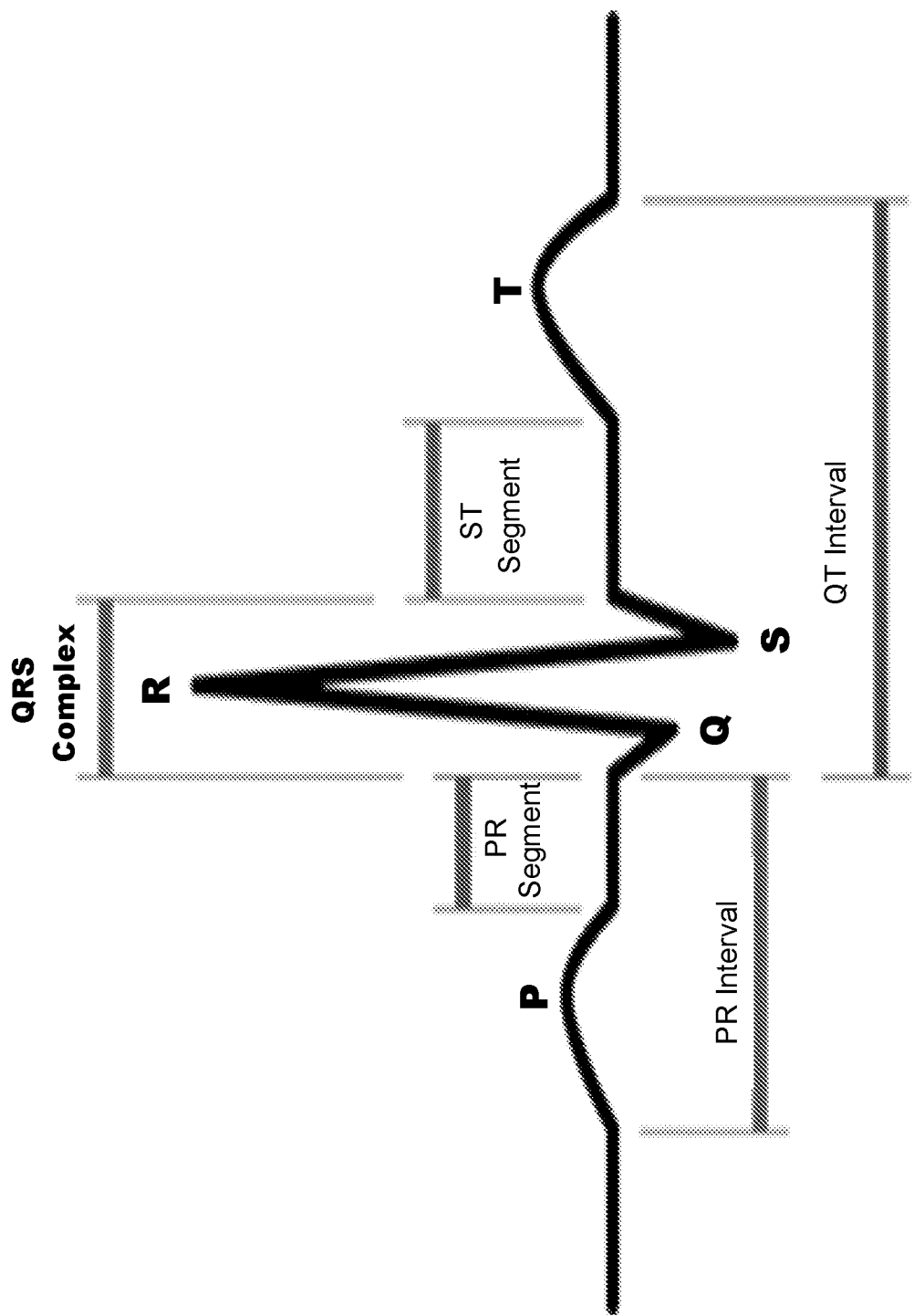
FIG. 22 illustrates an exemplary ECG wave illustrating the segments thereof.
Figure 24B:
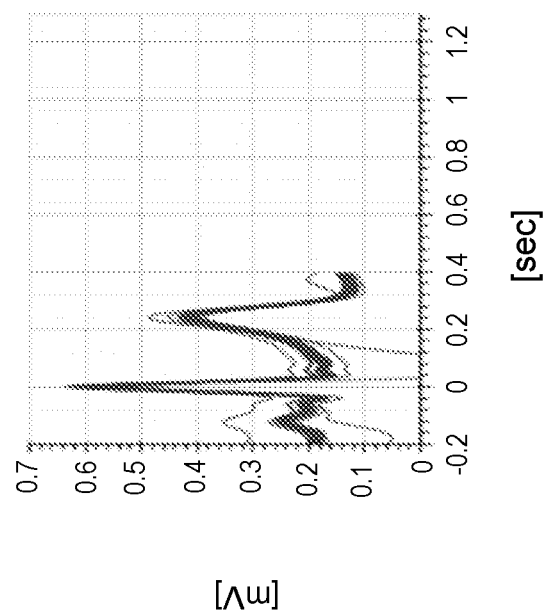
FIG. 24B illustrates a complex wave signature determined based on the ECG raw data of FIG. 24A.
Figure 24A:
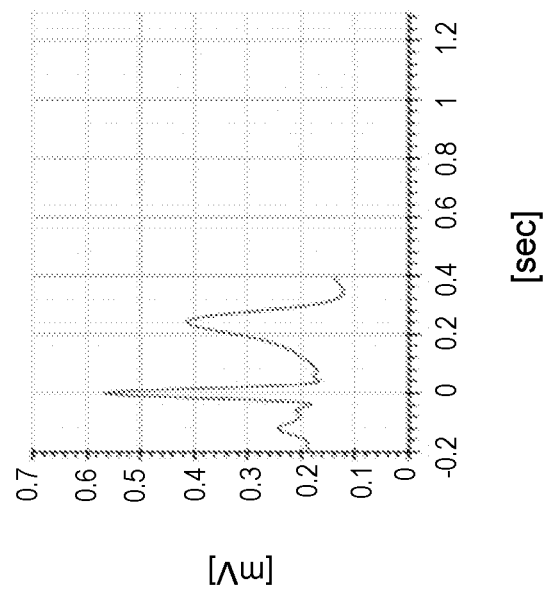
FIG. 24A illustrates a chart showing ECG raw data collected over a time interval.

In embodiments, where the monitor device 12, 112 is positioned closer to the heart, PWTT times will generally be shorter than if the device 12, 112 is positioned further from the heart regardless of the patient's blood pressure. Thus, the position of the device 12, 112 must be known in order to provide accurate measurements of blood pressure based on PWTT. In embodiments, the ECG complex wave signature may be used to identify the position of the monitor device 12, 112. In embodiments, the ECG complex wave signature may be based on the median of all ECG raw data provided over a 0.6 second time interval from a point that is 0.2 seconds prior to the R peak and ending 0.4 second after the R peak. As can be seen in FIG. 22, the R peak is the peak of electrical activity in the heart and is indicated by a peak in the ECG. It is preceded by a minimum Q and followed by another minimum S. A lower peak P precedes the Peak R and a Peak T that follows it. FIG. 24A illustrates the ECG raw data provided over the 0.6 second time interval. FIG. 24B illustrates the ECG complex wave signature based on the ECG raw data illustrated in FIG. 24A.

Figure 25:
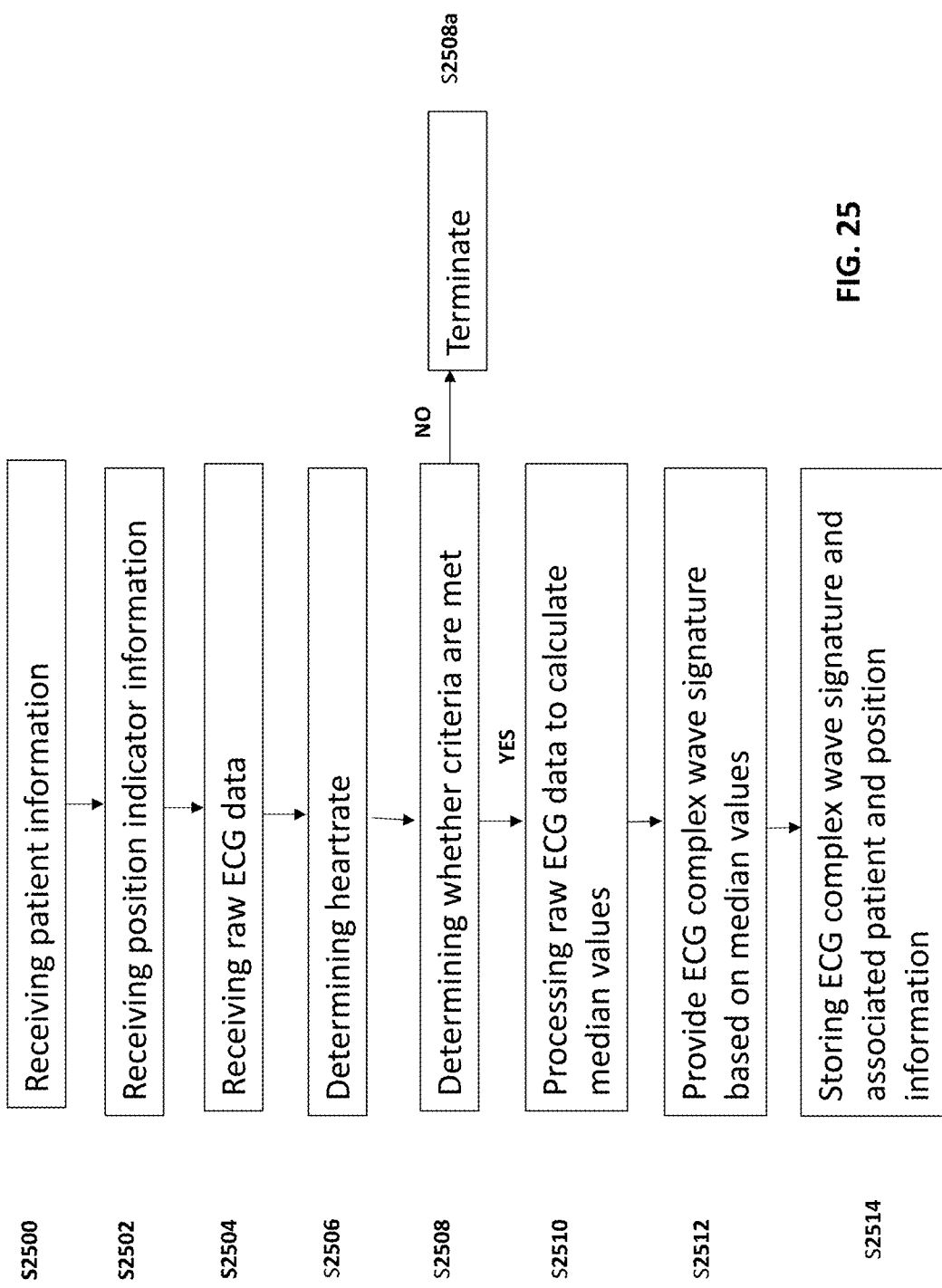
FIG. 25 illustrates an exemplary flow chart of a method of determining a complex wave signature.

FIG. 25 illustrates an exemplary flow chart showing a method for determining an ECG complex wave signature. In embodiments, at step S2500, patient identification information may be received uniquely identifying a patient. At step S2502, position indicator information may be received and indicates a present location of the monitor device 12, 112. In embodiments, the position indicator information may be provided by a user. In embodiments, at step S2504, raw ECG data may be received from the monitor device 12, 112. At step S2506, a heartrate may be determined based on the ECG raw data. At step S2508, a determination is made as to whether certain criteria regarding the heartrate have been met. In embodiments, this criterial may include that the heartrate is lower than 125 bps. In embodiments a higher or lower heartrate threshold may be used. In embodiments, the criteria may include a requirement that the heartrate of the patient be consistent with a normal sinus rhythm (NSR). In embodiments, if the criteria are not met, at step S2508a, an alert may be issued and the process may stop. Otherwise, at step S2510, the ECG raw data may be processed to determine the R Peaks and calculate the median values during the 0.6 second period discussed above. At step S2512, the median values are used to provide the ECG complex wave signature. At step S2514, the ECG complex wave signature may be associated with the patient identification information and position information and stored in one or more memory. In embodiments, the method of FIG. 25 may be implemented by any one of the monitor device 12, 112, the gateway device 14, the central monitor 16. In embodiments, the method of FIG. 25 may be implemented by one or more servers or computer systems operably connected to any one of the monitor device 12, 112, the gateway device 14, the central monitor 16.

Figure 26:
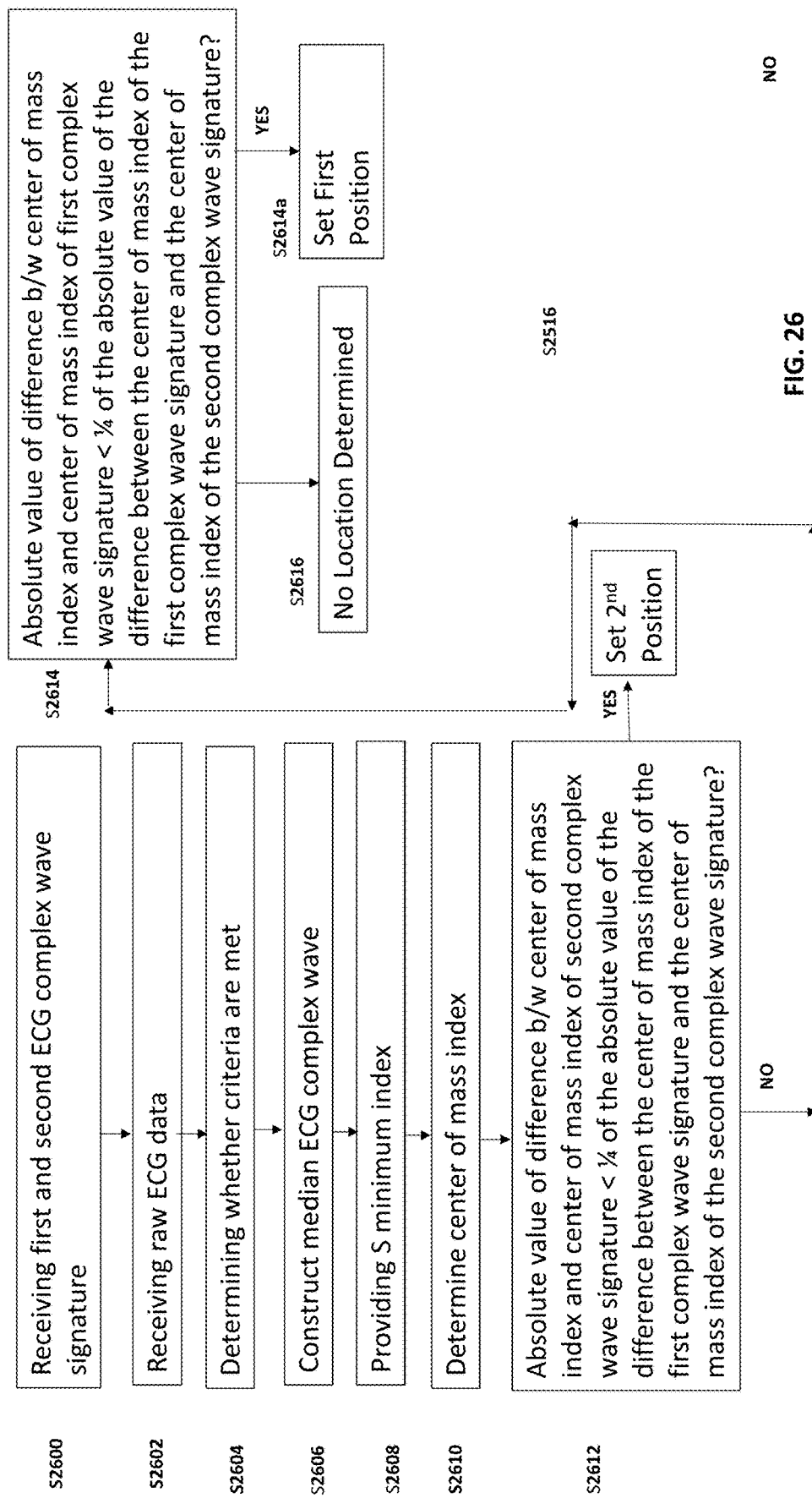
FIG. 26 illustrates an exemplary flow chart of a method of identifying a position of a monitor device based on complex wave signature.

In embodiments, the ECG complex wave signature may be used to determine the position of the monitor device 12, 112 on the patient's body automatically based on the ECG raw data. FIG. 26 illustrates an exemplary flow chart of a method for automatically determining the monitor device position. FIG. 26 illustrates an exemplary method to determine whether the monitor device 12, 112 is provided at one of two positions, however, the method would be applicable to determine a position from among additional positions as well. In embodiments, the method may begin at step S2600 by receiving a first ECG complex wave signature associated with a first position (mid chest for example) and a second ECG complex wave signature associated with a second position (left side of chest, for example). In embodiments, this information may be retrieved from one of more memory elements that are included in or operably connected to any one of the monitor device 12, 112, the gateway device 14 or the central monitor 16. In embodiments, step S2600 may include generation of a request for the first and second ECG complex wave signatures. In embodiments, at step S2602, the raw ECG data may be received from the monitor device 12, 112. At step S2604, a determination may be made as to whether the raw ECG data meets certain criteria. In embodiments, these criteria may be the same as those discussed above with respect to FIG. 25. That is, these criteria may include confirm that the heartrate does not exceed a certain threshold (125, for example) and that the heart is beating in a normal sinus rhythm. In embodiments, if the criteria are not met, at step S2604a, the process may be terminated. Otherwise, at step S2606, a median ECG complex is constructed based on the current raw ECG data in a manner similar to that discussed above with respect to FIG. 25. At step, S2608, an S minimum index is provided based on the raw ECG data where each S minimum follows the Peak P. At step S2610, a center of mass index is determined from the S minimum to the end of the 0.6 second interval for the raw ECG data. In addition, a center of mass index may be calculated for the first ECG complex wave signature and the second ECG complex wave signature. In embodiments, where F is a non-negative discrete function from a set of all-natural numbers between N to M and M>=N, the center of mass index of F, CM(F) is defined by the center of mass and an S minimum and may be calculated using the below equation:

$$CM(F) = (int) \frac{\sum_{i=N}^{M}(i*F(i))}{\sum_{i=N}^{M} F(i)}$$

Figures 27A, 27B:
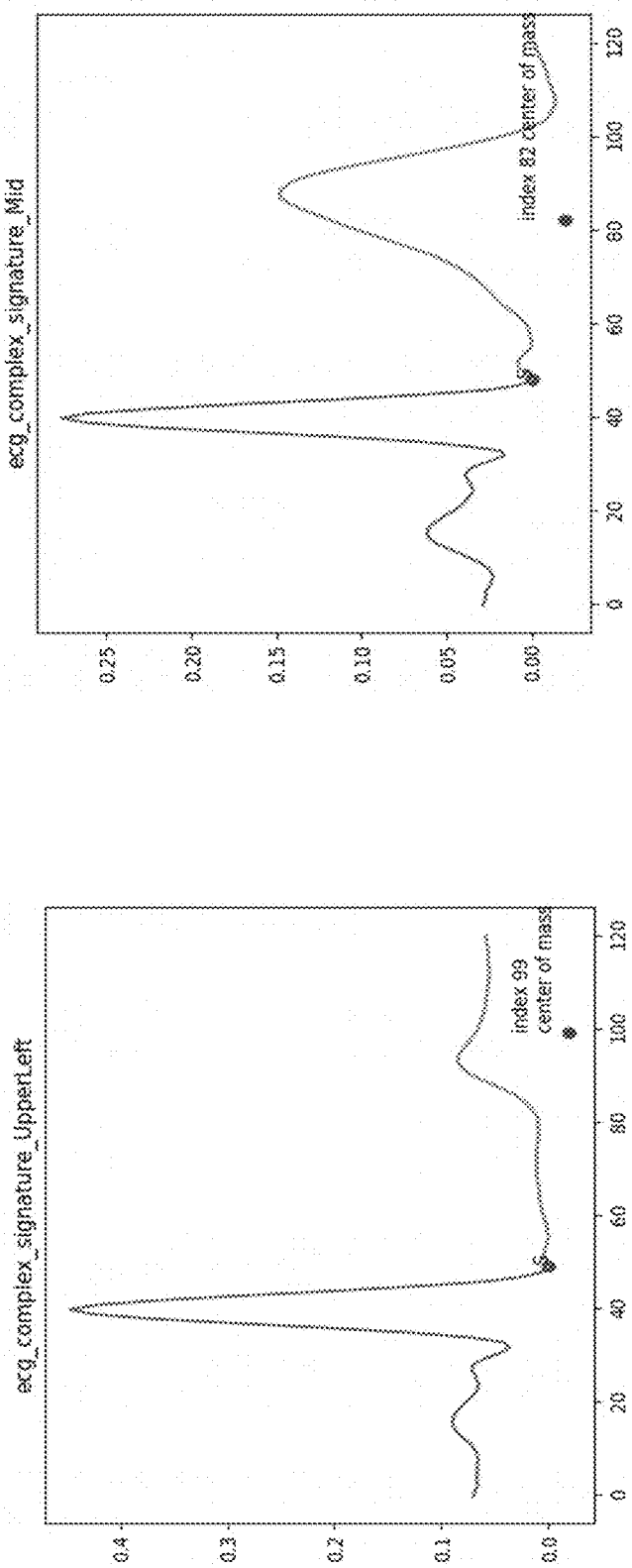
FIG. 27A illustrates an exemplary center of mass of a complex wave signature corresponding to an upper left chest position.

FIG. 27A illustrates an exemplary center of mass for the first ECG complex wave signature, which, in this illustration, corresponds to a positioning of the monitor device 12, 122 on the upper left chest. FIG. 27B illustrates an exemplary center of mass for the second ECG complex wave signature which, in this illustration, corresponds to a positioning of the monitor device 12, 122 on the middle of the chest. In embodiments, at step S2612, a determination is made as to whether the absolute value of the difference between the center of mass index and the center of mass index of the center of mass index of the second complex wave signature is less than ¼ of the absolute value of the difference between the center of mass index of the first complex wave signature and the center of mass index of the second complex wave signature. If so, the current position is the second position associated with the second complex wave signature as indicated at step S2612a. Otherwise, at step S2614, a determination is made as to whether the absolute value of the difference between the center of mass index and the center of mass index of the first complex wave signature is less than ¼ of the absolute value of the difference between the center of mass of the first complex wave signature and the center of mass index of the second complex wave signature. If so, YES at step S2614a, the position of the monitor device is determined as the first position corresponding to the first complex wave signature (upper left). Otherwise, NO at step S2614, at step S2616 an alert may be provided to indicate that the position of the monitor device 12, 112 cannot be determined. In such cases, the monitor device 12, 112 may need to be repositioned to provide reliable blood pressure information. FIG. 26 provides an example of identifying a position from a choice of two positions. In embodiments, the method of FIG. 26 may be expanded to allow for identification of more than two positions as well. In embodiments, each position may be associated with a corresponding complex wave signature, which may be provided using the method described above with reference to FIG. 25. These complex wave signatures may be compared to complex wave signatures provided based on the present raw ECG in the manner described above to determine the position at which the raw ECG data is collected. In embodiments, the monitor device 12, 112 may be positioned virtually anywhere on a patient's body and a corresponding complex wave signature may be provided for each location using the method of FIG. 25, for example. In embodiments, the monitor device 12, 112 is positioned on the torso of the patient and a corresponding complex wave signature may be determined and stored in the manner describe din FIG. 25, for example and retrieved or otherwise accessed or provided in the method of FIG. 26 to identify the location of the device 12, 112. In embodiments, the positions used may be based on clinical considerations or other medical needs.

In embodiments, the monitor device 12, 112 provides a single device that captures ECG raw data, PPG raw data, patient movement information and skin temperature information. In embodiments, the calculation of blood pressure may take place in the device 12, 112, the gateway device 14 or the central monitor 16, for example. In embodiments, communication between the device 112, the gateway device 14 and the central monitoring station 16 may be bidirectional such that data may be provided from the monitor device 112 to the gateway device 14 or central monitoring station 16 and data or instructions may be provided to the monitor device 112 from the central monitoring station 16 and the central monitoring station 16. In embodiments, communication may take place via Bluetooth, a local gateway (such as gateway device 114), cellular or GSM. In embodiments, the device 112 may include a rechargeable battery, which may be recharged via the cradle 50 and the contacts 140, for example. In embodiments, the device 112 may include a single use battery.

In embodiments, the monitor device 12, 112 may be connected to an electrode pad P, as noted above. In embodiments, the monitor device 12, 112 may perform the needed data collection with a minimum footprint using the pad—about 10 cm from end to end (see FIG. 17C-17D, for example). In embodiments, data may be collected on a continuous basis or on an on-demand basis. In embodiments, as noted above, communication between the monitor device 12, 112 and the gateway device 14 and/or the central monitor 16 may be bidirectional. In embodiments, the electrode pad may include adhesive such that it stays in place on the patient's body. In embodiments, the device 12, 112 may be attached, via a magnet to the electrode pad or to a belt secured to the user's body. In embodiments, the monitor device 12, 112 may be provided on a belt that is wrapped around the patient's body.

Figure 19C:
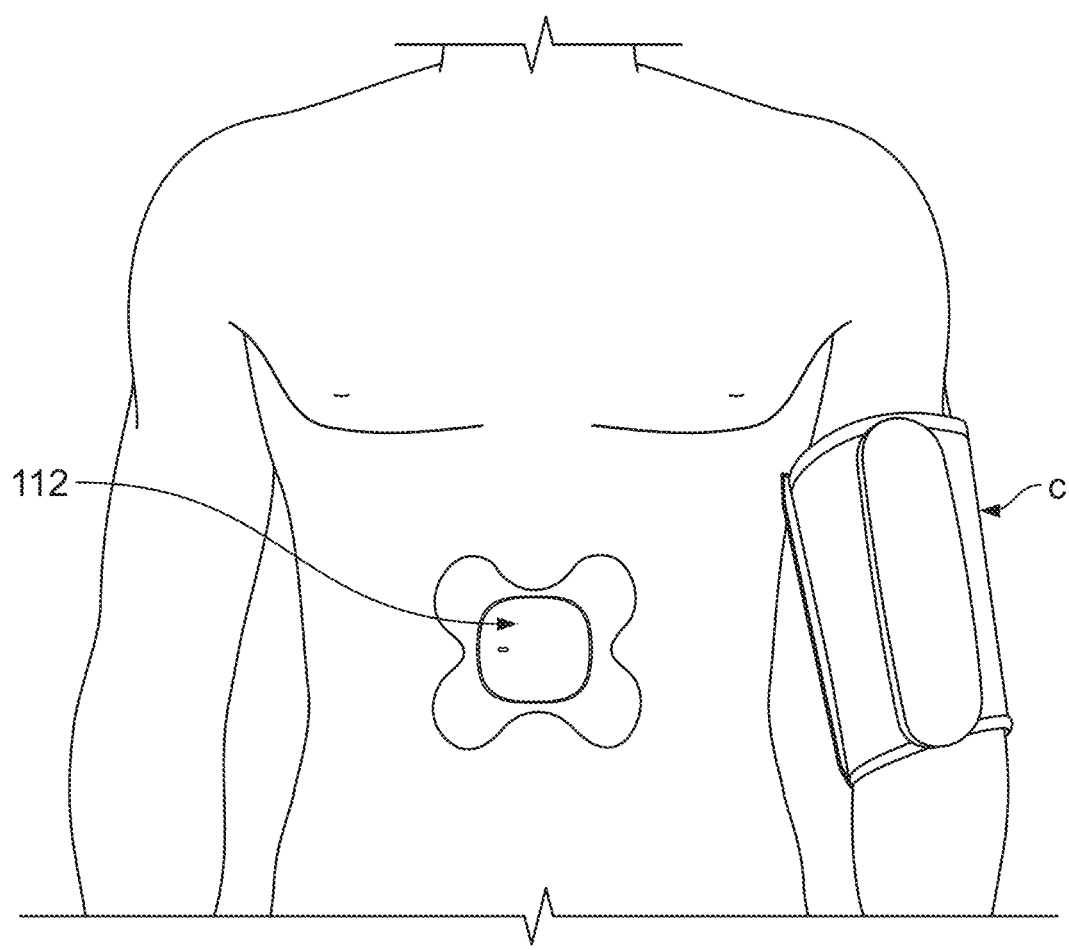
FIG. 19C illustrated an exemplary positioning of the monitor device of FIGS. 17A-17B and a digital cuff sphygmomanometer used in calibration.

FIG. 19 illustrates a schematic representation of the monitor device 12, 112 and a cuff C used in conjunction with a digital sphygmomanometer C to provide the systolic/diastolic blood pressure measurement that is received and stored.

FIG. 20 illustrates a flowchart showing an exemplary calibration method for determining blood pressure based on PWTT using data collected by the monitor device 12, 112. In step S2000, a calibration mode may be initiated. In embodiments, this may be done based on instructions provided from the gateway device 14 or the central monitor 16. In embodiments, the instructions may be based on input provided by a user, physician or other health professional. In embodiments, the instructions may be provided periodically or aperiodically by one or more of the gateway device 14 or central monitor 16 based on a calibration schedule.

In step S2002 connections between the monitor device 12, 112, digital sphygmomanometer C, gateway device 14 and/or central station 16 may be established and confirmed. After the connections are confirmed, in step S2004, data is collected by the device 12, 112 and the digital sphygmomanometer C and may be provided to the gateway device 14 and/or central station 16. In embodiments, the data collected from the device 12, 112 may include the ECG raw data and the PPG raw data. In embodiments, data from other sensors may be collected, for example, skin temperature information. In embodiments, systolic/diastolic data may be collected using the digital sphygmomanometer C (in mmHg) and provided to the gateway device 14 and/or the central monitor station 16. In embodiments, the digital sphygmomanometer C may also collect data related to heartbeat. If the connection is not confirmed in step S2002, an error message or other error indication may be provided. The error indication may be provided to the gateway device 14 or the central station 16. In embodiments, the error indication may be displayed on the gateway device 14 or the central monitor 16. In embodiments, the error message may be stored such that a record of the connection failure may be maintained.

In embodiments, after the connection is confirmed in step S2002 and before data collection begins in step S2004, there may be an additional step of checking for a test cancel signal or message. If detected, the calibration run may be stopped. In embodiments, after the connection is confirmed in step S2002 and before data collection begins in step S2004, a countdown to the beginning of the test may be generated and displayed, preferably on the gateway device 14. In embodiments, the gateway device 14 may be a mobile electronic device such as smart phone, tablet computer or other computer system. In embodiments, this countdown may be provided on a display of the device 112. In embodiments, this countdown may be provided on the display D of the digital sphygmomanometer C.

In embodiments, after the connection is confirmed in step S2002 and before data collection begins in step S2004, the gateway device 14 may generate and send start signals to the device 12, 112 and the digital sphygmomanometer C to begin data collection. In embodiments, after the data is collected, it is checked for errors in step S2006. As noted above, errors may be indicated where a heartrate exceeds a certain threshold or where the heartrate is irregular. When no errors are detected, the collected data may be packaged along with the test/calibration identification information, the time stamp, body orientation information and movement information and stored in a memory in step S2008. In embodiments, the packaging may be performed at the device 12, 112, the gateway device 14 or the central station monitor 16. In embodiments, the packaged data may be sent to the gateway device 14 or the central station 16 from the monitor device 12, 112.

In embodiments, the calibration coefficients discussed above may be calculated using the packaged data in step S2010. This may be done at the gateway device 14, central station 16 or another server or computer system in communication therewith. In embodiments, this step may include checking the calculated calibration coefficients for errors. In embodiments, certain coefficient thresholds, for example, minimum and/or maximum values or a range, may be established, for example, by a physician or other health professional. In embodiments, the calculated calibration coefficients may be compared to the thresholds. In embodiments, in the event that a calculated calibration coefficient falls outside of the threshold(s), this may indicate that there was an error in calculation. In embodiments, if there is an error, an error message may be generated and sent to one or more of the device 12, 112, the gateway 14, the central station monitor 16 or another operatively connected computer system, to name a few. In embodiments, the error alert may be stored with any data that is generated using the coefficients. In embodiments, the central station monitor 16 may store the collected data and the calculated coefficients. In embodiments, the information may be saved as part of a patient record associated with a particular patient. In embodiments, the patient information may be accessed by any of the device 12, 112, the gateway device 14 or the central station 16. In embodiments, the patient information may be stored in the device 12, 112, the gateway device 14 or the central station monitor 16 or a memory device operatively connected thereto. FIG. 21 discussed above discussed an exemplary method of calculating the calibration coefficients.

In embodiments, as noted above, PWTT values may change according to position of the device 12, 112. In general, for a given ECG measurement, the calculated PWTT value will be shorter if the distance between the sensor and the heart is shorter than it would be if the distance were longer. Thus, the coefficient values used for estimated systolic blood pressure SBP and the estimated diastolic blood pressure DBP may be different depending on sensor position for each person. Thus, it is important to be able to remotely and automatically determine the position of the monitor device 12, 112 on the user's body. Further, a method of locating the position of the device 12, 112 provides confirmation that the device has been properly positioned and thus may avoid human error.

In embodiments, the position of the device 12, 112, may be determined based on machine vision. In embodiments, finding the position may include capturing an image template signature during the calibration measurements. Examples of these image templates can be found in FIGS. 28A, 28B and 28C. In embodiments, the templates may correspond to the complex digital signatures discussed above. In embodiments, the complex wave signature may be captured as a photograph or a video. In embodiments, the ECG data may be obtained and stored as an image or video. In embodiments, identification of position may be accomplished based on a visual analysis of the complex wave signatures. In embodiments, the visual analysis may include the identification of peaks and unique characteristic of the complex digital signatures. In embodiments, these features may be used to match current ECG data to one or more of the signatures based on a visual matching similar to that used in facial recognition, for example.

Although the present invention has been described in relation to particular embodiments thereof, many other variations and modifications and other uses will become apparent to those skilled in the art. Steps and units described in relation to one aspect of the method or system may be added, or substituted, for steps or units described with respect to another aspect of the system. Combinations and permutations of steps different from those outlined are also contemplated. Steps outlined in sequence need not necessarily be performed in sequence, not all steps need necessarily be executed, and other intervening steps may be inserted. It is preferred, therefore, that the present invention be limited not by the specific disclosure herein.

What is claimed is:

1. A method of calibrating a system for determining blood pressure based on pulse wave transit time comprising:
    initiating, by a gateway device, a calibration mode;
    establishing, by the gateway device, a first connection between the gateway device and a monitoring device mounted on a body of a patient;
    establishing, by the gateway device, a second connection between the gateway device and a digital sphygmomanometer;
    receiving, by the gateway device, first collected data from the monitor device, wherein the first collected data includes ECG raw data and PPG raw data;
    receiving, by the gateway device, second collected data from the digital sphygmomanometer, wherein the second collected data includes systolic/diastolic pressure information indicative of a blood pressure of the patient obtained using a cuff positioned on the patient's body;
    checking, by the gateway device, the first collected data and the second collected data for errors;
    packaging, by the gateway device, the first collected data and the second collected data with other data, wherein the other data includes at least a time stamp;
    calculating, by the gateway device, one or more calibration coefficients based on the first collected data, second collected data and the other data wherein the calculating step includes:
        using a first linear equation associated with a systolic pressure number to determine the one or more calibration coefficients; and
        using a second linear equation associated with a diastolic pressure number to determine the one or more coefficients; and
    storing, by the gateway device, the one or more calibration coefficients in a memory operatively connected to the gateway device.

2. The method of claim 1, wherein the step of checking the first collected data and the second collected data for errors includes:
    confirming that a heartrate indicated by the first collected data and second collected data is below a threshold level.

3. The method of claim 1, wherein the step of checking the first collected data and the second collected data for errors includes:
    confirming that a heart rhythm indicated by the first collected data and the second collected data corresponds to a normal sinus rhythm.

4. The method of claim 1, wherein the time stamp is provided by at least one of the monitor device and the gateway device.

5. The method of claim 1, wherein the one or more calibrations coefficients are stored in the memory and are uniquely associated with the patient.

6. The method of claim 5, further comprising:
providing, by the gateway device, a patient record uniquely associated with the patient, wherein the patient record includes the first collected data, the second collected data, the other data and the one or more coefficients; and
storing, by the gateway device, the patient record in the memory.

7. The method of claim 1, further comprising:
providing, by the gateway device, a patient record uniquely associated with the patient, wherein the patient record includes the first collected data, the second collected data, the other information and the one or more calibration coefficients; and
storing, by the gateway device, the patient record in the memory.

8. The method of claim 7, wherein the patient record includes position information associated with the one or more coefficients, wherein the position information is associated with a position of the monitor device when the first data is collected.

9. The method of claim 8, wherein the position information is based on a complex wave signature associated with the first collected data.

10. The method of claim 8, wherein the complex wave signature is associated with ECG data provided by the monitor device.

11. The method of claim 8, wherein the complex wave signature is associated with a position identifier indicating a specific position of the monitor device.

* * * * *